(12) United States Patent
Stoeckius

(10) Patent No.: US 12,365,942 B2
(45) Date of Patent: Jul. 22, 2025

(54) METHODS OF DECREASING BACKGROUND ON A SPATIAL ARRAY

(71) Applicant: 10X Genomics, Inc., Pleasanton, CA (US)

(72) Inventor: Marlon Stoeckius, Stockholm (CH)

(73) Assignee: 10x Genomics, Inc., Pleasanton, CA (US)

( * ) Notice: Subject to any disclaimer, the term of this patent is extended or adjusted under 35 U.S.C. 154(b) by 202 days.

(21) Appl. No.: 17/147,874

(22) Filed: Jan. 13, 2021

(65) Prior Publication Data

US 2021/0214785 A1 Jul. 15, 2021

Related U.S. Application Data

(60) Provisional application No. 62/960,573, filed on Jan. 13, 2020.

(51) Int. Cl.
*C12Q 1/6874* (2018.01)
*C12Q 1/6837* (2018.01)

(52) U.S. Cl.
CPC ......... *C12Q 1/6874* (2013.01); *C12Q 1/6837* (2013.01)

(58) Field of Classification Search
CPC ... C12Q 1/6837; C12Q 1/6874; C12Q 1/6841
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,883,867 A | 11/1989 | Lee | |
| 4,965,188 A | 10/1990 | Mullis | |
| 4,988,617 A | 1/1991 | Landegren et al. | |
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |
| 5,410,030 A | 4/1995 | Yue | |
| 5,436,134 A | 7/1995 | Haugland | |
| 5,455,166 A | 10/1995 | Walker | |
| 5,487,972 A | 1/1996 | Gelfand et al. | |
| 5,494,810 A | 2/1996 | Barany et al. | |
| 5,503,980 A | 4/1996 | Cantor | |
| 5,512,439 A | 4/1996 | Hornes | |
| 5,512,462 A | 4/1996 | Cheng | |
| 5,582,977 A | 12/1996 | Yue | |
| 5,599,675 A | 2/1997 | Brenner | |
| 5,641,658 A | 6/1997 | Adams | |
| 5,648,245 A | 7/1997 | Fire et al. | |
| 5,658,751 A | 8/1997 | Yue | |
| 5,695,940 A | 12/1997 | Drmanac et al. | |
| 5,750,341 A | 5/1998 | Macevicz | |
| 5,763,175 A | 6/1998 | Brenner | |
| 5,830,711 A | 11/1998 | Barany et al. | |
| 5,837,832 A | 11/1998 | Chee et al. | |
| 5,854,033 A | 12/1998 | Lizardi | |
| 5,863,753 A | 1/1999 | Haugland | |
| 5,871,921 A | 2/1999 | Landegren et al. | |
| 5,912,148 A | 6/1999 | Eggerding | |
| 5,925,545 A | 7/1999 | Reznikoff et al. | |
| 5,928,906 A | 7/1999 | Koester et al. | |
| 5,958,775 A | 9/1999 | Wickstrrom | |
| 5,962,271 A | 10/1999 | Chenchik et al. | |
| 5,962,272 A | 10/1999 | Chenchik et al. | |
| 5,965,443 A | 10/1999 | Reznikoff et al. | |
| 6,013,440 A | 1/2000 | Lipshutz | |
| 6,027,889 A | 2/2000 | Barany et al. | |
| 6,054,274 A | 4/2000 | Sampson et al. | |
| 6,060,240 A | 5/2000 | Kamb et al. | |
| 6,130,073 A | 10/2000 | Eggerding | |
| 6,143,496 A | 11/2000 | Brown | |
| 6,153,389 A | 11/2000 | Haarer | |
| 6,159,736 A | 12/2000 | Reznikoff et al. | |
| 6,165,714 A | 12/2000 | Lane et al. | |
| 6,210,891 B1 | 4/2001 | Nyren | |
| 6,210,894 B1 | 4/2001 | Brennan | |
| 6,214,587 B1 | 4/2001 | Dattagupta | |
| 6,251,639 B1 | 6/2001 | Kurn | |
| 6,258,568 B1 | 7/2001 | Nyren | |
| 6,266,459 B1 | 7/2001 | Walt | |
| 6,268,148 B1 | 7/2001 | Barany et al. | |
| 6,274,320 B1 | 8/2001 | Rothberg | |
| 6,291,180 B1 | 9/2001 | Chu | |
| 6,291,187 B1 | 9/2001 | Kingsmore et al. | |
| 6,300,063 B1 | 10/2001 | Lipshutz et al. | |
| 6,309,824 B1 | 10/2001 | Drmanac | |
| 6,323,009 B1 | 11/2001 | Lasken et al. | |
| 6,344,316 B1 | 2/2002 | Lockhart | |
| 6,344,329 B1 | 2/2002 | Lizardi et al. | |
| 6,355,431 B1 | 3/2002 | Chee | |
| 6,368,801 B1 | 4/2002 | Faruqi | |
| 6,401,267 B1 | 6/2002 | Drmanac | |
| 6,404,907 B1 | 6/2002 | Gilchrist | |
| 6,432,360 B1 | 8/2002 | Church et al. | |
| 6,503,713 B1 | 1/2003 | Rana | |
| 6,506,561 B1 | 1/2003 | Cheval et al. | |
| 6,534,266 B1 | 3/2003 | Singer | |
| 6,544,732 B1 | 4/2003 | Chee | |
| 6,573,043 B1 | 6/2003 | Coben et al. | |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Chen, Yunlong, et al. "Arrayed profiling of multiple glycans on whole living cell surfaces." Analytical chemistry 85.22 (2013): 11153-11158 (Year: 2013).*

(Continued)

*Primary Examiner* — Anne M. Gussow
*Assistant Examiner* — Alexandra Geraldine Dace Denito
(74) *Attorney, Agent, or Firm* — Fish & Richardson P.C.

(57) ABSTRACT

Provided herein are methods of determining a location of a target analyte in a non-permeabilized biological sample and methods of reducing background binding of an analyte on an array.

20 Claims, 1 Drawing Sheet
(1 of 1 Drawing Sheet(s) Filed in Color)

(56) References Cited

U.S. PATENT DOCUMENTS

| | | |
|---|---|---|
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsubashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |

(56) References Cited

U.S. PATENT DOCUMENTS

| | | |
|---|---|---|
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,662,468 B2 | 5/2020 | Chee |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,001,879 B1 | 5/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,214,796 B2 | 1/2022 | Shirai et al. |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,459,607 B1 | 10/2022 | Terry et al. |
| 11,479,809 B2 | 10/2022 | Frisen et al. |
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,713,480 B2 | 8/2023 | Lee |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |

(56) References Cited

U.S. PATENT DOCUMENTS

| | | |
|---|---|---|
| 12,024,741 B2 | 7/2024 | Tentori et al. |
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 12,128,403 B2 | 10/2024 | Kim et al. |
| 12,129,516 B2 | 10/2024 | Tentori et al. |
| 12,157,124 B2 | 12/2024 | Cox et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0241660 A1 | 12/2004 | Wojtowicz et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1 | 2/2006 | Bauer et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0270273 A1 | 10/2009 | Burns et al. |
| 2009/0283407 A1 | 11/2009 | Van Eijk |
| 2009/0286249 A1 | 11/2009 | Bekcer et al. |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastba et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |

(56) References Cited

U.S. PATENT DOCUMENTS

| | | |
|---|---|---|
| 2013/0035239 A1 | 2/2013 | Kong et al. |
| 2013/0040842 A1 | 2/2013 | Lim et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0283860 A1 | 4/2017 | Kool et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0052082 A1* | 2/2018 | Groll ................ G01N 35/1011 |
| 2018/0057873 A1 | 3/2018 | Zhou et al. |
| 2018/0080019 A1 | 3/2018 | Blainey et al. |
| 2018/0088112 A1 | 3/2018 | Fan et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0334670 A1 | 11/2018 | Bharadwaj et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0167576 A1* | 6/2019 | Schachar ............ A61K 31/495 |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1* | 7/2019 | Frisen et al. ......... C12Q 1/6834 |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |

(56) References Cited

U.S. PATENT DOCUMENTS

| | | |
|---|---|---|
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava et al. |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |

(56) References Cited

U.S. PATENT DOCUMENTS

| | | |
|---|---|---|
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |
| 2024/0279747 A1 | 8/2024 | Williams |
| 2024/0287600 A1 | 8/2024 | Iyer et al. |
| 2024/0294971 A1 | 9/2024 | Galonska |
| 2024/0294974 A1 | 9/2024 | Galonska et al. |
| 2024/0294975 A1 | 9/2024 | Lin et al. |
| 2024/0301488 A1 | 9/2024 | Stoeckius |
| 2024/0301489 A1 | 9/2024 | Chew et al. |
| 2024/0360494 A1 | 10/2024 | Costa et al. |
| 2024/0368711 A1 | 11/2024 | Giacomello et al. |
| 2024/0377297 A1 | 11/2024 | Cox et al. |
| 2024/0385088 A1 | 11/2024 | Kim et al. |
| 2024/0392349 A1 | 11/2024 | Frisen et al. |
| 2024/0392351 A1 | 11/2024 | Chee |
| 2024/0392352 A1 | 11/2024 | Stahl et al. |
| 2024/0392353 A1 | 11/2024 | Engblom et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2130913 | 12/2009 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/17390 | 3/2000 |
| WO | WO 2001/06012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2009/032167 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |

(56) References Cited

FOREIGN PATENT DOCUMENTS

| | | |
|---|---|---|
| WO | WO 2011/008502 | 1/2011 |
| WO | WO 2011/062933 | 5/2011 |
| WO | WO 2011/068088 | 6/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |

(56) References Cited

FOREIGN PATENT DOCUMENTS

| | | |
|---|---|---|
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |

OTHER PUBLICATIONS

Ludeck, E. et al. "Single-cell in situ RNA profiling by sequential hybridization". Nature Methods, vol. 11, No. 4 (Apr. 2014), pp. 360-361. (Year: 2014).*

Ludeck, E. et al. Supplemental Information. Nature Methods, vol. 11, No. 4 (Apr. 2014), pp. 360-361. (Year: 2014).*

Li, F. et al. "Multifunctional Poly-N-Isopropylacrylamide / DNAzyme microgels as highly efficient and recyclable catalysts for biosensing". Advanced Functional Materials, vol. 28 (2018), p. 1705876. (Year: 2018).*

Asp et al., "Spatially Resolved Transcriptomes-Next Generation Tools for Tissue Exploration," Bioessays, Oct. 2020, 42(10):e1900221, 16 pages.

Balakrishnan et al., "Flap endonuclease 1," Annu Rev Biochem., Jun. 2013, 82:119-138.

Bergenstråhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15):2911-2914.

Blair et al., "Microarray temperature optimization using hybridization kinetics," Methods Mol Biol., 2009. 529:171-96.

Bolotin et al., "MiXCR: software for comprehensive adaptive immunity profiling," Nat Methods., May 2015. 12(5):380-1.

Chen et al., "Parallel single nucleotide polymorphism genotyping by surface invasive cleavage with universal detection," Anal Chem., Apr. 2005, 77(8):2400-5.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Ciaccio et al., "Systems analysis of EGF receptor signaling dynamics with microwestern arrays," Nat Methods, Feb. 2010, 7(2):148-55.

Gerard et al., "Excess dNTPs minimize RNA hydrolysis during reverse transcription," Biotechniques, Nov. 2002, 33(5):984, 986, 988, 990.

Hessner et al., "Genotyping of factor V G1691A (Leiden) without the use of PCR by invasive cleavage of oligonucleotide probes," Clin Chem., Aug. 2000, 46(8 Pt 1):1051-6.

Hoffman et al., "Formaldehyde crosslinking: a tool for the study of chromatin complexes," J Biol Chem., Oct. 2015, 290(44):26404-11.

Hughes et al., "Microfluidic Western blotting," PNAS, Dec. 2012, 109(52):21450-21455.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Nilsson et al., "RNA-templated DNA ligation for transcript analysis," Nucleic Acids Res., Jan. 2001, 29(2):578-81.

Olivier, "The Invader assay for SNP genotyping," Mutat. Res., Jun. 2005, 573(1-2):103-110.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Picelli et al., "Full-length RNA-seq from single cells using Smart-seq2," Nat Protoc., Jan. 2014, 9(1):171-81.

Schouten et al., "Relative quantification of 40 nucleic acid sequences by multiplex ligation-dependent probe amplification," Nucleic Acids Res., Jun. 2002, 30(12):e57, 13 pages.

Singh et al., "High-throughput targeted long-read single cell sequencing reveals the clonal and transcriptional landscape of lymphocytes," Nat Commun., Jul. 2019, 10(1):3120, 13 pages.

Sountoulidis et al., "SCRINSHOT, a spatial method for single-cell resolution mapping of cell states in tissue sections." PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

Sutherland et al., "Utility of formaldehyde cross-linking and mass spectrometry in the study of protein-protein interactions," J. Mass Spectrom., Jun. 2008, 43(6):699-715.

Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

Tu et al., "TCR sequencing paired with massively parallel 3' RNA-seq reveals clonotypic T cell signatures," Nature Immunology, Dec. 2019, 20(12):1692-1699.

Vázquez Bernat et al., "High-Quality Library Preparation for NGS-Based Immunoglobulin Germline Gene Inference and Repertoire Expression Analysis," Front Immunol., Apr. 2019, 10:660, 12 pages.

Wu et al., "RollFISH achieves robust quantification of single-molecule RNA biomarkers in paraffin-embedded tumor tissue samples." Commun Biol., Nov. 2018, 1:209, 8 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/

(56) References Cited

OTHER PUBLICATIONS

4q03w6959AJFxffSw5lee9/6a2ac61cf6388a72564eeb96bc294967/ CG000238_VisiumSpatialTissueOptimizationUserGuide_Rev_A. pdf>, 46 pages.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.

Cruz et al., "Methylation in cell-free DNA for early cancer detection," Ann Oncol., Jun. 2018, 29(6):1351-1353.

Hamaguchi et al., "Direct reverse transcription-PCR on oligo(dT)-immobilized polypropylene microplates after capturing total mRNA from crude cell lysates," Clin Chem., Nov. 1998, 44(11):2256-63.

Ke et al., "In situ sequencing for RNA analysis in preserved tissue and cells," Nat Methods., Sep. 2013, Supplementary Materials, 29 pages.

Miner et al., "Molecular barcodes detect redundancy and contamination in hairpin-bisulfite PCR," Nucleic Acids Res., Sep. 2004, 32(17):e135, 4 pages.

Wang et al., "Tagmentation-based whole-genome bisulfite sequencing," Nature Protocols, Oct. 2013, 8(10):2022-2032.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Boulé et al., "Terminal deoxynucleotidyl transferase indiscriminately incorporates ribonucleotides and deoxyribonucleotides," J Biol Chem., Aug. 2001, 276(33):31388-93.

Burgess, "Spatial transcriptomics coming of age," Nat Rev Genet., Jun. 2019, 20(6):317, 1 page.

Caliari et al., "A practical guide to hydrogels for cell culture," Nat Methods., Apr. 2016, 13(5):405-14.

Evers et al., "The effect of formaldehyde fixation on RNA: optimization of formaldehyde adduct removal, " J Mol Diagn., May 2011, 13(3):282-8.

Gansauge et al., "Single-stranded DNA library preparation from highly degraded DNA using T4 DNA ligase, " Nucleic Acids Res., Jun. 2017, 45(10):e79, 10 pages.

Hafner et al., "Identification of microRNAs and other small regulatory RNAs using cDNA library sequencing," Methods, Jan. 2008, 44(1):3-12.

Hanauer et al., "Separation of nanoparticles by gel electrophoresis according to size and shape," Nano Lett., Sep. 2007, 7(9):2881-5.

Ho et al., "Characterization of an ATP-Dependent DNA Ligase Encoded by Chlorella Virus PBCV-1," Journal of Virology, Mar. 1997, 71(3):1931-1937.

Hsuih et al., "Novel, Ligation-Dependent PCR Assay for Detection of Hepatitis C Virus in Serum," Journal of Clinical Microbiology, Mar. 1996, 34(3):501-507.

Kumar et al., "Template-directed oligonucleotide strand ligation, covalent intramolecular DNA circularization and catenation using click chemistry," J Am Chem Soc., May 2007, 129(21):6859-64.

Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.

Mulder et al., "CapTCR-seq: hybrid capture for T-cell receptor repertoire profiling," Blood Advances, Dec. 2018, 2(23):3506-3514.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Ozsolak et al., "Digital transcriptome profiling from attomole-level RNA samples," Genome Res., Apr. 2010, 20(4):519-25.

Slomovic et al., "Addition of poly(A) and poly(A)-rich tails during RNA degradation in the cytoplasm of human cells," Proc Natl Acad Sci USA, Apr. 2010, 107(16):7407-12.

Ulery et al., "Biomedical Applications of Biodegradable Polymers," J Polym Sci B Polym Phys., Jun. 2011, 49(12):832-864.

Vandenbroucke et al., "Quantification of splice variants using real-time PCR," Nucleic Acids Research, 2001, 29(13):e68, 7 pages.

Wang et al., "Optimization of Process Conditions for Infected Animal Tissues by Alkaline Hydrolysis Technology," Procedia Environmental Sciences, 2016, 31:366-374.

Zhang et al., "Genome-wide open chromatin regions and their effects on the regulation of silk protein genes in Bombyx mori," Sci Rep., Oct. 2017, 7(1):12919, 9 pages.

Hayes et al., "Electrophoresis of proteins and nucleic acids: I-Theory," BMJ, Sep. 1989, 299(6703):843-6.

Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.

Zahra et al., "Assessment of Different Permeabilization Methods of Minimizing Damage to the Adherent Cells for Detection of Intracellular RNA by Flow Cytometry, " Avicenna Journal of Medical Biotechnology, Jan. 1, 2014, 6(1):38-46.

Appella, "Non-natural nucleic acids for synthetic biology," Current Opinion in Chemical Biology, Dec. 2009, 13(5-6): 687-696.

Bunt et al., "FRET from single to multiplexed signaling events," Biophys Rev. Apr. 2017, 9(2): 119-129.

Grünweller et al., "Locked Nucleic Acid Oligonucleotides," BioDrugs, Jul. 2007, 21(4): 235-243.

Gu et al., "Multiplex single-molecule interaction profiling of DNA-barcoded proteins," Nature, Sep. 21, 2014, 515:554-557.

Ma et al., "Isothermal amplification method for next-generation sequencing," PNAS, Aug. 12, 2013, 110(35):14320-14323.

Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.

[No Author Listed], "Chromium Next GEM Single Cell 3' Reagent Kits v3.1 (Dual Index)—User Guide," 10x Genomics, Mar. 2021, Document No. CG000315, 61 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/ 5UJrN0CH17rEk0UXwd19It/e54d99fb08a8f1500aba503005a04a56/ CG000238_VisiumSpatialTissueOptimizationUserGuide_RevD. pdf>, 43 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/ 3GGIfH3RWpd1bFVha1pexR/8baa08d9007157592b65b2cdc7130990/ CG000239_VisiumSpatialGeneExpression_UserGuide_RevD. pdf>, 70 pages.

Blanco et al., "A practical approach to FRET-based PNA fluorescence in situ hybridization," Methods, Dec. 2010, 52(4):343-51.

Czarnik, "Encoding methods for combinatorial chemistry," Curr Opin Chem Biol., Jun. 1997, 1(1):60-6.

Macbeath et al., "Printing proteins as microarrays for high-throughput function determination," Science, Sep. 2000, 289(5485):1760-1763.

Morlan et al., "Selective depletion of rRNA enables whole transcriptome profiling of archival fixed tissue." PLoS One, Aug. 2012, 7(8):e42882, 8 pages.

Pellestor et al., "The peptide nucleic acids (PNAs), powerful tools for molecular genetics and cytogenetics," Eur J Hum Genet., Sep. 2004, 12(9):694-700.

Aran et al., "xCell: digitally portraying the tissue cellular heterogeneity landscape," Genome Biol., Nov. 2017, 18(1):220, 14 pages.

Plongthongkum et al., "Advances in the profiling of DNA modifications: cytosine methylation and beyond," Nature Reviews Genetics, Aug. 2014, 15(10):647-661.

Salmén et al., "Barcoded solid-phase RNA capture for Spatial Transcriptomics profiling in mammalian tissue sections," Nature Protocols, Oct. 2018, 13(11):2501-2534.

Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/ documents/documentation/chemistry_documentation/ribosomal-depletion/ribo-zero/ribo-zero-reference-guide-15066012-02.pdf>, 36 pages.

(56) References Cited

OTHER PUBLICATIONS

Niedringhaus et al., "Landscape of next-generation sequencing technologies," Anal Chem., Jun. 2011, 83(12):4327-41.
Qiu et al., "Combination probes with intercalating anchors and proximal fluorophores for DNA and RNA detection," Nucleic Acids Research, Sep. 2016, 44(17):e138, 12 pages.
Zhao et al., "Isothermal Amplification of Nucleic Acids," Chemical Reviews, Nov. 2015, 115(22):12491-12545.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Fu et al., "Repeat subtraction-mediated sequence capture from a complex genome," Plant J., Jun. 2010. 62(5):898-909.
Ganguli et al., "Pixelated spatial gene expression analysis from tissue," Nat Commun., Jan. 2018, 9(1):202, 9 pages.
Habnke et al., "Striptease on glass: validation of an improved stripping procedure for in situ microarrays," J Biotechnol., Jan. 2007, 128(1):1-13.
Hu et al., "High reproducibility using sodium hydroxide-stripped long oligonucleotide DNA microarrays," Biotechniques, Jan. 2005, 38(1):121-4.
Lee et al., "Improving the efficiency of genomic loci capture using oligonucleotide arrays for high throughput resequencing," BMC Genomics, Dec. 2009, 10:646, 12 pages.
Alam, "Proximity Ligation Assay (PLA)," Curr Protoc Immunol., Nov. 2018, 123(1):e58, 8 pages.
Li et al., "An activity-dependent proximity ligation platform for spatially resolved quantification of active enzymes in single cells," Nat Commun, Nov. 2017, 8(1):1775, 12 pages.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Wang et al., "Imaging-based pooled CRISPR screening reveals regulators of lncRNA localization," Proc Natl Acad Sci USA, May 2019, 116(22):10842-10851.
Wiedmann et al., "Ligase chain reaction (LCR)—overview and applications," PCR Methods Appl., Feb. 1994, 3(4):S51-64.
U.S. Appl. No. 60/416,118, filed Oct. 3, 2002, Fan et al..
U.S. Appl. No. 61/267,363, filed Dec. 7, 2009, Fan et al.
[No Author Listed], "Chromium Next GEM Single Cell 3' Reagent Kits v3.1," User Guide, Document No. CG000204, 10x Genomics, Nov. 2019, 58 pages.
[No Author Listed], "HuSNP Mapping Assay User's Manual," Affymetrix Part No. 90094 (Affymetrix, Santa Clara, Calif.), GeneChip, 2000, 104 pages.
[No. Author Listed], "Microarray technologies have excellent possibilities in genomics-related researches," Science Tools From Amersham Pharmacia Biotech, 1998, 3(4): 8 pages (with English Translation).
[No. Author Listed], "Proseek® Multiplex 96x96 User Manual," Olink Proteomics, Olink Bioscience, Uppsala, Sweden, 2017, 20 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592665b2cdc7130990/CG000239_VisiumSpatialGeneExpression_UserGuide_RevD.pdf>, 70 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.
Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Andresen et al., "Helicase-dependent amplification; use in OnChip amplification and potential for point-of-care diagnostics," Expert Rev Mol Diagn., Oct. 2009, 9(7):645-650.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration; structure of the initial covalent product and its precursor, and a role for the viral IN protein," Proc Natl Acad Sci USA, Apr. 1989, 86(8):2525-9.

(56) References Cited

OTHER PUBLICATIONS

Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem, J. 2006, 398(1):135-144.
Burgess, "A space for transcriptomics," Nature Reviews Genetics, 2016, 17(8):436-7.
Burgess, "Finding structure in gene expression, " Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "µCB-seq: microfluidic cell barcoding and sequencing for high-resolution imaging and sequencing of single cells," Lab Chip, Nov. 2020, 20(21):3899-3913.
Chrisey et al., "Covalent attachment of synthetic DNA to self-assembled monolayer films," Nucleic Acids Res., Aug. 1996, 24(15):3031-9.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):253-264.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.

Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009. 6(4):263-65.
Duncan et al., "Affinity chromatography of a sequence-specific DNA binding protein using Teflon- linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides." Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Continuous Polony Gels for Tissue Mapping with High Resolution and R.NA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://geneaarrays.com/services/microarrays/illumina/beadarray-technology/>, [retrieved on Jan. 30, 2020], 3 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.

(56) References Cited

OTHER PUBLICATIONS

Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008. 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pd f>, 3 pages.
Ichikawa et al., "In vitro transposition of transposon Tn3," J Biol. Chem., Nov. 1990. 265(31):18829-32, Abstract.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases." Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1):173-86.

Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.

(56) References Cited

OTHER PUBLICATIONS

Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing." PLoS One, Apr. 2010, 5(4):e10029, 7 pages.
Lyck et al., "Immunohistochemical markers for quantitative studies of neurons and glia in human neocortex," J Histochem Cytochem, 2008, 56(3):201-21.
MacIntyre, "Unmasking antigens for immunohistochemistry.," Br J Biomed Sci., 2001, 58(3):190-6.
Marx, "Method of the Year: spatially resolved transcriptomics," Nature Methods, 2021, 18(1):9-14.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans—chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad, Sci. USA, May 2003, 100(10):5926-5931.
Mizusawa et al.. "A bacteriophage lambda vector for cloning with BamHI and Sau3A, " Gene, 1982, 20(3):317-322.
Motea et al., "Terminal deoxynucleotidyl transferase: the story of a misguided DNA polymerase," Biochim Biophys Acta., May 2010, 1804(5):1151-66.
Nandakumar et al., "How an RNA Ligase Discriminates RNA versus DNA Damage," Molecular Cell, 2004, 16:211-221.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "TnS transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tcl/mariner transposon family," Curr Top Microbiol Immunol., 1996, 204:125-43.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate, " Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Saxonov et al., "10x Genomics, Mastering Biology to Advance Human Health, " PowerPoint, 10x, 2020, 41 pages.
Schena et al., "Quantitative monitoring of gene expression patterns with a complementary DNA microarray," Science, Oct. 1995, 270(5235):467-470.
Schweitzer et al., "Multiplexed protein profiling on microarrays by rolling-circle amplification," Nature Biotechnology, Apr. 2002, 20(4):359-365.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741): 1728-1732.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.

(56) References Cited

OTHER PUBLICATIONS

Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993. 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nature Methods, 2019, 9 pages.
Vincent et al., "Helicase-dependent isothermal DNA amplification," EMBO Rep., Aug. 2004, 5(8):795-800.
Viollet et al., "T4 Rna ligase 2 truncated active site mutants; improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.

Weinreich et al., "Evidence that the cis Preference of the Tn5 Transposase is Caused by Nonproductive Multimerization," Genes and Development, Oct. 1994, 8(19):2363-2374.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archacal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
U.S. Appl. No. 16/353,937, Frisen et al., filed Mar. 14, 2019.
U.S. Appl. No. 17/707,189, Chell et al., filed Mar. 29, 2022.
Dalma-Weiszhausz et al., "The affymetrix GeneChip platform: an overview," Methods Enzymol., 2006. 410:3-28.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Lahiani et al., "Enabling Histopathological Annotations on Immunofluorescent Images through Virtualization of Hematoxylin and Eosin," J Pathol Inform., Feb. 2018, 9:1, 8 pages.
Lou et al., "A review of room temperature storage of biospecimen tissue and nucleic acids for anatomic pathology laboratories and biorepositories," Clin Biochem., Mar. 2014, 47(4-5):267-73.
Lykidis et al., "Novel zinc-based fixative for high quality DNA, RNA and protein analysis," Nucleic Acids Res., Jun. 2007, 35(12):e85, 10 pages.
Miller et al., "Chapter 11—Solid and Suspension Microarrays for Microbial Diagnostics," Methods in Microbiology, 2015, 42:395-431.
Nadji et al., "Immunohistochemistry of tissue prepared by a molecular-friendly fixation and processing system," Appl Immunohistochem Mol Morphol., Sep. 2005, 13(3):277-82.

(56) References Cited

OTHER PUBLICATIONS

Passow et al., "RNAlater and flash freezing storage methods nonrandomly influence observed gene expression in RNAseq experiments," bioRxiv, Jul. 2018, 28 pages.
Porreca et al., "Polony DNA sequencing," Curr Protoc Mol Biol., Nov. 2006, Chapter 7, Unit 7.8, pp. 7.8.1-7.8.22.
Vickovic et al., "SM-Omics: An automated Platform for High-Throughput Spatial Multi-Omics," bioRxiv, Oct. 2020, 40 pages.
Wohnhaas et al., "DMSO cryopreservation is the method of choice to preserve cells for droplet-based single-cell RNA sequencing," Scientific Reports, Jul. 2019, 9(1):10699, 14 pages.
U.S. Appl. No. 63/033,348, filed Jun. 2, 2020, Bent.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Baner et al., "Signal amplification of padlock probes by rolling circle replication," Nucleic Acids Res., 1998, 26(22):5073-5078.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Chen et al., "Efficient in situ barcode sequencing using padlock probe-based BaristaSeq," Nucleic Acids Res., 2018, 46(4): e22, 11 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Codeluppi et al., "Spatial organization of the somatosensory cortex revealed by osmFISH," Nature Methods, Nov. 2018, 15:932-935.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Faruqi et al., "High-throughput genotyping of single nucleotide polymorphisms with rolling circle amplification," BMC Genomics, Aug. 2001, 2:4, 10 pages.
Gao et al., "A highly homogeneous expansion microscopy polymer composed of tetrahedron-like monomers," bioRxiv, Oct. 22, 2019, 23 pages (Preprint).
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Goh et al., "Highly Specific Multiplexed RNA Imaging In Tissues With Split-FISH," Nat Methods, Jun. 15, 2020, 17(7):689-693, 21 pages.
Goransson et al., "A single molecule array for digital targeted molecular analyses," Nucleic Acids Res., Nov. 25, 2009, 37(1):e7, 9 pages.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Mignardi et al., "Oligonucleotide gap-fill ligation for mutation detection and sequencing in situ," Nucleic Acids Research, Aug. 3, 2015, 43(22):e151, 12 pages.

Mohsen et al., "The Discovery of Rolling Circle Amplification and Rolling Circle Transcription," Acc Chem Res., Nov. 15, 2016, 49(11):2540-2550, 25 pages.
Nallur et al., "Signal amplification by rolling circle amplification on DNA microarrays," Nucleic Acids Res., Dec. 1, 2001, 29(23):e118, 9 pages.
Raj et al., "Imaging individual mRNA molecules using multiple singly labeled probes," Nature Methods, Oct. 2008, 5(10):877-879, 9 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Takei et al., "Integrated Spatial Genomics Reveals Global Architecture Of Single Nuclei," Nature, Jan. 27, 2021, 590(7845):344-350, 53 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Schmidl et al., "ChIPmentation: fast, robust, low-input ChIP-seq for histones and transcription factors," Nature Methods, Oct. 2015, 12:963-965.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Hobro et al., "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Su et al., "Restriction enzyme selection dictates detection range sensitivity in chromatin conformation capture-based variant-to-gene mapping approaches," bioRxiv, Dec. 15, 2020, 22 pages.
Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
Kuhn et al., "A novel, high-performance random array platform for quantitative gene expression profiling," Genome Res, 2004, 14:2347-2356.
Bibikova et al., "Quantitative gene expression profiling in formalin-fixed paraffin-embedded tissues using universal bead arrays," The American Journal of Pathology, Nov. 1, 2004, 165(5):1799-1807.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.

(56) References Cited

OTHER PUBLICATIONS

Sun et al., "Statistical Analysis of Spatial Expression Pattern for Spatially Resolved Transcriptomic Studies," Nature Methods, Jan. 27, 2020, 17(2): 193-200.

Svensson et al., "SpatialDE: identification of spatially variable genes," Nature Methods, May 2018, 15:343-346, 15 pages.

Asp et al., "A spatiotemporal organ-wide gene expression and cell atlas of the developing human heart," Cell, Dec. 12, 2019, 179(7):1647-1660.

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial- gene-expression-fresh-frozen/documentation/steps/library-construction/visium-spatial-gene-expression-reagent-kits-user-guide>, 71 pages.

Nelson, "The Most Popular Cutting Styles of Gaskets & Their Advantages," Grand River Rubber & Plastics Blog, Feb. 18, 2020, retrieved on Dec. 3, 2024, retreived from URL <https://www.info.grrp.com/blog/the-most-popular-cutting-styles-of-gaskets-their-advantages>, 4 pages.

* cited by examiner

METHODS OF DECREASING BACKGROUND ON A SPATIAL ARRAY

CROSS-REFERENCE TO RELATED APPLICATIONS

This application claims priority under 35 U.S.C. § 119 (e) to U.S. Provisional Patent Application Ser. No. 62/960,573, filed on Jan. 13, 2020, the entire contents of which are hereby incorporated by reference.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

SUMMARY

This application provides for an improvement between signal to noise (e.g., background analyte binding) during performance of any of the methods described herein for determining a location of a target analyte in a biological sample.

Provided herein are methods for decreasing background binding of a target nucleic acid on an array that include: (a) disposing a biological sample onto an array; in some embodiments, the array has a first area covered by the biological sample and a second area not covered by the biological sample; in some embodiments, the array comprises a plurality of capture probes; in some embodiments, a capture probe of the plurality of capture probes comprises a spatial barcode and a capture domain; (b) contacting the second area of the array with a solution comprising a diffusion-restricted nuclease, (c) removing the diffusion-restricted nuclease from the second area of the array; and (d) permeabilizing the biological sample, such that the capture domain binds to the target nucleic acid in the first area, thereby decreasing the background binding of a target nucleic acid on the array.

In some embodiments of any of the methods described herein, the methods further include determining (i) all or a portion of the sequence of the spatial barcode, or a complement thereof, and (ii) all or a portion of the sequence of the target nucleic acid, or a complement thereof, and using the sequences of (i) and (ii) to determine the location of the target nucleic acid in the biological sample.

In some embodiments of any of the methods described herein, the diffusion-restricted nuclease degrades single-stranded nucleic acids. In some embodiments of any of the methods described herein, the diffusion-restricted nuclease degrades double-stranded nucleic acids.

In some embodiments of any of the methods described herein, the diffusion-restricted nuclease is covalently linked to a bead, a particle, or a polymer. In some embodiments of any of the methods described herein, the polymer is a polyethylene glycol.

In some embodiments of any of the methods described herein, the diffusion-restricted nuclease is an endonuclease or an exonuclease. In some embodiments of any of the methods described herein, the exonuclease is a 3' to 5' exonuclease. In some embodiments of any of the methods described herein, the exonuclease is a DNAse.

In some embodiments of any of the methods described herein, the removing comprises washing.

In some embodiments of any of the methods described herein, the array comprises a slide. In some embodiments of any of the methods described herein, the array is a bead array.

In some embodiments of any of the methods described herein, the determining comprises sequencing (i) all or a portion of the sequence of the spatial barcode, or a complement thereof, and (ii) all or a portion of the sequence of the target nucleic acid, or a complement thereof. In some embodiments of any of the methods described herein, the sequencing is high throughput sequencing.

In some embodiments of any of the methods described herein, the determining comprises extending the capture probe using the target nucleic acid as the template.

In some embodiments of any of the methods described herein, steps (a) and (b) are performed at substantially the same time.

Also provided herein are methods for determining a location of a target nucleic acid in a biological sample disposed onto an array, where the array has a first area covered by the biological sample and a second area not covered by the biological sample, where the array comprises a plurality of capture probes, where a capture probe of the plurality of capture probes comprises a spatial barcode and a capture domain, wherein the methods include: (a) contacting the second area of the array with a solution comprising a diffusion-restricted nuclease; (b) removing the diffusion-restricted nuclease from the second area of the array; (c) permeabilizing the biological sample, such that the capture domain binds to the target nucleic acid; and (d) determining (i) all or a portion of the sequence of the spatial barcode, or a complement thereof, and (ii) all or a portion of the sequence of the target nucleic acid, or a complement thereof, and using the sequences of (i) and (ii) to determine the location of the target nucleic acid in the biological sample.

In some embodiments of any of the methods described herein, the diffusion-restricted nuclease degrades single-stranded nucleic acids. In some embodiments of any of the method described herein, the diffusion-restricted nuclease degrades double-stranded nucleic acids.

In some embodiments of any of the methods described herein, the diffusion-restricted nuclease is covalently linked to a bead, a particle, or a polymer. In some embodiments of the methods described herein, the polymer is a polyethylene glycol.

In some embodiments of any of the methods described herein, the diffusion-restricted nuclease is an endonuclease or an exonuclease. In some embodiments of any of the methods described herein, the exonuclease is a 3' to 5' exonuclease. In some embodiments of any of the methods described herein, the exonuclease is a DNAse.

In some embodiments of any of the methods described herein, the removing in step (b) comprises washing. In some embodiments of any of the methods described herein, the array comprises a slide. In some embodiments of any of the methods described herein, the array is a bead array.

In some embodiments of any of the methods described herein, the determining in step (d) comprises sequencing (i) all or a portion of the sequence of the spatial barcode, or a complement thereof, and (ii) all or a portion of the sequence of the target nucleic acid, or a complement thereof. In some embodiments of any of the methods described herein, the sequencing is high throughput sequencing.

In some embodiments of any of the methods described herein, the determining in step (d) includes extending the capture probe using the target nucleic acid as the template.

In some embodiments of any of the methods described herein, the biological sample is a tissue section. In some embodiments of any of the methods described herein, the tissue section is from a fresh frozen tissue section.

Also provided herein are methods for determining a location of a target analyte in a biological sample that include: (a) contacting a plurality of analyte capture agents to the biological sample; in some embodiments, an analyte capture agent of the plurality of analyte capture agents comprises an analyte binding moiety barcode, an analyte capture sequence, and an analyte binding moiety that binds specifically to the target analyte; (b) disposing the biological sample onto an array; in some embodiments, the array has a first area covered by the biological sample and a second area not covered by the biological sample; in some embodiments, the array comprises a plurality of capture probes; in some embodiments, a capture probe of the plurality comprises a spatial barcode and a capture domain that binds specifically to the analyte capture sequence; (c) contacting the second area of the array with a solution comprising a diffusion-restricted nuclease; (d) removing the diffusion-restricted nuclease from the second area of the array; and (e) determining (i) all or a portion of the sequence of the spatial barcode, or a complement thereof, and (ii) all or a portion of the sequence of the analyte binding moiety barcode, or a complement thereof, and using the sequences of (i) and (ii) to determine the location of the target analyte in the biological sample.

In some embodiments of any of the methods described herein, step (a) is performed before step (b). In some embodiments of any of the methods described herein, step (b) is performed before step (a).

In some embodiments of any of the methods described herein, the diffusion-restricted nuclease degrades single-stranded nucleic acids. In some embodiments of any of the methods described herein, the diffusion-restricted nuclease degrades double-stranded nucleic acids.

In some embodiments of any of the methods described herein, the diffusion-restricted nuclease is covalently linked to a bead, a particle, or a polymer. In some embodiments of any of the methods described herein, the polymer is a polyethylene glycol.

In some embodiments of any of the methods described herein, the diffusion-restricted nuclease is an endonuclease or an exonuclease. In some embodiments of any of the methods described herein, the exonuclease is a 3' to 5' exonuclease. In some embodiments of any of the methods described herein, the exonuclease is a DNAse.

In some embodiments of any of the methods described herein, the removing in step (d) comprises washing.

In some embodiments of any of the methods described herein, the array comprises a slide. In some embodiments of any of the methods described herein, the array is a bead array.

In some embodiments of any of the methods described herein, the determining in step (e) comprises sequencing (i) all or a portion of the sequence of the spatial barcode, or a complement thereof, and (ii) all or a portion of the sequence of the analyte binding moiety barcode, or a complement thereof. In some embodiments of any of the methods described herein, the sequencing is high throughput sequencing.

In some embodiments of any of the methods described herein, the determining in step (e) comprises extending the capture probe using the analyte binding moiety barcode as the template.

In some embodiments of any of the methods described herein, steps (a) and (b) are performed at substantially the same time.

In some embodiments of any of the methods described herein, the methods further include after step (d): permeabilizing the biological sample disposed on the array, such that the analyte binding moiety binds to the target analyte and the capture domain binds to the analyte capture sequence.

In some embodiments of any of the methods described herein, the biological sample is a tissue section. In some embodiments of any of the methods described herein, the tissue section is a fresh, frozen tissue section.

Also provided herein are kits that include an array comprising a plurality of capture probes, where a capture probe of the plurality of capture probes comprises a spatial barcode and a capture domain; and a diffusion-restricted nuclease.

Also provided herein are kits that include a plurality of analyte capture agents, where an analyte capture agent of the plurality of analyte capture agents comprises an analyte binding moiety barcode, an analyte capture sequence, and an analyte binding moiety; an array comprising a plurality of capture probes, where a capture probe of the plurality of capture probes comprises a spatial barcode and a capture domain; and a diffusion-restricted nuclease.

As used herein, the term "non-permeabilized biological sample" means a biological sample that has not been exposed to one or more permeabilizing agents (e.g., any of the exemplary permeabilizing agents described herein), or has not been subjected to a permeabilization method (e.g., any of the exemplary permeabilization methods described herein).

As used herein, the term "diffusion-restricted nuclease" means a nuclease that has is covalently and/or non-covalently attached to an agent that results in a decrease in the rate of diffusion of the nuclease as compared to the rate of diffusion of the same nuclease not covalently or non-covalently attached to the agent. In some embodiments, a diffusion-restricted nuclease is not able to significantly pass through an intact plasma membrane of a non-permeabilized mammalian cell.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The patent or application file contains at least one drawing executed in color. Copies of this patent or patent application publication with color drawing(s) will be provided by the Office upon request and payment of the necessary fee.

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
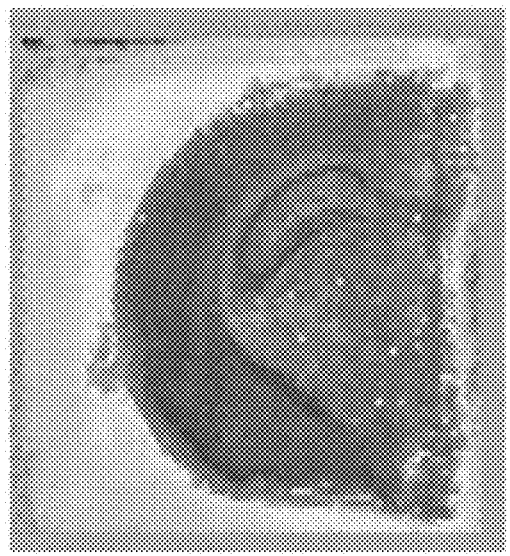
FIG. 1 shows an example of background signal resulting from RNA in an area of an array where a brain tissue sample had not been placed.

The methods described herein provide for an improvement between signal to background during performance of any of the methods described herein for determining a location of a target analyte in a biological sample.

Provided herein are methods for determining a location of a target nucleic acid in a biological sample disposed onto an array, where the array has a first area covered by the biological sample and a second area not covered by the biological sample, where the array comprises a plurality of capture probes, where a capture probe of the plurality of capture probes comprises a spatial barcode and a capture domain, where the methods include: (a) contacting the second area of the array with a solution comprising a diffusion-restricted nuclease; (b) removing the diffusion-restricted nuclease from the second area of the array; (c) permeabilizing the biological sample, such that the capture domain binds to the target nucleic acid; and (d) determining (i) all or a portion of the sequence of the spatial barcode, or a complement thereof, and (ii) all or a portion of the sequence of the target nucleic acid, or a complement thereof, and using the sequences of (i) and (ii) to determine the location of the target nucleic acid in the biological sample.

Provided herein are methods for determining a location of a target analyte in a biological sample that include: (a) contacting a plurality of analyte capture agents to the biological sample, where an analyte capture agent of the plurality of analyte capture agents comprises an analyte binding moiety barcode, an analyte capture sequence, and an analyte binding moiety that binds specifically to the target analyte; (b) disposing the biological sample onto an array, where the array has a first area covered by the biological sample and a second area not covered by the biological sample, where the array comprises a plurality of capture probes, where a capture probe of the plurality comprises a spatial barcode and a capture domain that binds to the analyte capture sequence; (c) contacting the second area of the array with a solution comprising a diffusion-restricted nuclease; (d) removing the diffusion-restricted nuclease from the second area of the array; and (e) determining (i) all or a portion of the sequence of the spatial barcode, or a complement thereof, and (ii) all or a portion of the sequence of the analyte binding moiety barcode, or a complement thereof, and using the sequences of (i) and (ii) to determine the location of the target analyte in the biological sample.

Provided herein are methods for decreasing background binding of a target nucleic acid on an array that include: (a) disposing a biological sample onto an array, where the array has a first area covered by the biological sample and a second area not covered by the biological sample, where the array comprises a plurality of capture probes, where a capture probe of the plurality of capture probes comprises a spatial barcode and a capture domain; (b) contacting the second area of the array with a solution comprising a diffusion-restricted nuclease, (c) removing the diffusion-restricted nuclease from the second area of the array; and (d) permeabilizing the biological sample, such that the capture domain binds to the target nucleic acid in the first area, thereby decreasing the background binding of a target nucleic acid on the array.

Provided herein are kits that include: an array comprising a plurality of capture probes, where a capture probe of the plurality of capture probes comprises a spatial barcode and a capture domain; and a diffusion-restricted nuclease.

Provided herein are kits that include: a plurality of analyte capture agents, where an analyte capture agent of the plurality of analyte capture agents comprises an analyte binding moiety barcode, an analyte capture sequence, and an analyte binding moiety; an array comprising a plurality of capture probes, where a capture probe of the plurality of capture probes comprises a spatial barcode and a capture domain; and a diffusion-restricted nuclease.

Some embodiments of any of the methods described herein can provide for at least a 0.1-fold improvement, at least a 0.5-fold improvement, at least a 0.8-fold improvement, at least a 1-fold improvement, at least a 1.5-fold improvement, at least a 2-fold improvement, at least a 2.5-fold improvement, at least a 3-fold improvement, at least a 3.5-fold improvement, at least a 4-fold improvement, at least a 4.5-fold improvement, at least a 5-fold improvement, at least a 5.5-fold improvement, at least a 6-fold improvement, at least a 6.5-fold improvement, at least a 7-fold improvement, at least a 7.5-fold improvement, at least a 8-fold improvement, at least a 8.5-fold improvement, at least a 9-fold improvement, at least a 9.5-fold improvement, at least 10-fold improvement, at least a 15-fold improvement, at least a 20-fold improvement, at least 30-fold improvement, at least 50-fold improvement, or at least 100-fold improvement in the signal to noise ratio as compared to a similar method performed without the use of a diffusion-restricted nuclease. See, e.g., FIG. 1 and FIG. 2.

Some embodiments of any of the methods described herein can provide for about a 0.1-fold improvement to about a 100-fold improvement, about a 0.1-fold improvement to about a 50-fold improvement, about a 0.1-fold improvement to about a 30-fold improvement, about a 0.1-fold improvement to about a 20-fold improvement, about a 0.1-fold improvement to about a 15-fold improvement, about a 0.1-fold improvement to about a 10-fold improvement, about a 0.1-fold improvement to about a 8-fold improvement, about a 0.1-fold improvement to about a 6-fold improvement, about a 0.1-fold improvement to about a 4-fold improvement, about a 0.1-fold improvement to about a 2-fold improvement, about a 0.1-fold improvement to about a 1-fold improvement, about a 0.1-fold improvement to about a 0.8-fold improvement, about a 0.1-fold improvement to about a 0.6-fold improvement, about a 0.1-fold improvement to about a 0.4-fold improvement, about a 0.1-fold improvement to about a 0.2-fold improvement, about a 0.2-fold improvement to about a 100-fold improvement, about a 0.2-fold improvement to about a 50-fold improvement, about a 0.2-fold improvement to about a 30-fold improvement, about a 0.2-fold improvement to about a 20-fold improvement, about a 0.2-fold improvement to about a 15-fold improvement, about a 0.2-fold improvement to about a 10-fold improvement, about a 0.2-fold improvement to about a 8-fold improvement, about a 0.2-fold improvement to about a 6-fold improvement, about a 0.2-fold improvement to about a 4-fold improvement, about a 0.2-fold improvement to about a 2-fold improvement, about a 0.2-fold improvement to about a 1-fold improvement, about a 0.2-fold improvement to about a 0.8-fold improvement, about a 0.2-fold improvement to about a 0.6-fold improvement, about a 0.2-fold improvement to about a 0.4-fold improvement, about a 0.4-fold improvement to about a 100-fold improvement, about a 0.4-fold improvement to about a 50-fold improvement, about a 0.4-fold improvement to about a 30-fold improvement, about a 0.4-fold improvement to about a 20-fold improvement, about a 0.4-fold improvement to about a 15-fold improvement, about a 0.4-fold improvement to about a 10-fold improvement, about a 0.4-fold improvement to about a 8-fold improvement, about a 0.4-fold improvement to about a 6-fold improvement, about a 0.4-fold improvement to about a 4-fold improvement, about a 0.4-fold improvement to about a 2-fold improvement, about a 0.4-fold improvement to about a 1-fold improvement, about a 0.4-fold improvement to about a 0.8-fold improvement, about a 0.4-fold improvement to about a 0.6-fold improvement, about a 0.6-fold improvement to about a 100-fold improvement, about a 0.6-fold improvement to about a 50-fold improvement, about a 0.6-fold improvement to about a 30-fold improvement, about a 0.6-fold improvement to about a 20-fold improvement, about a 0.6-fold improvement to about a 15-fold improvement, about a 0.6-fold improvement to about a 10-fold improvement, about a 0.6-fold improvement to about a 8-fold improvement, about a 0.6-fold improvement to about a 6-fold improvement, about a 0.6-fold improvement to about a 4-fold improvement, about a 0.6-fold improvement to about a 2-fold improvement, about a 0.6-fold improvement to about a 1-fold improvement, about a 0.6-fold improvement to about a 0.8-fold improvement, about a 0.8-fold improvement to about a 100-fold improvement, about a 0.8-fold improvement to about a 50-fold improvement, about a 0.8-fold improvement to about a 30-fold improvement, about a 0.8-fold improvement to about a 20-fold improvement, about a 0.8-fold improvement to about a 15-fold improvement, about a 0.8-fold improvement to about a 10-fold improvement, about a 0.8-fold improvement to about a 8-fold improvement, about a 0.8-fold improvement to about a 6-fold improvement, about a 0.8-fold improvement to about a 4-fold improvement, about a 0.8-fold improvement to about a 2-fold improvement, about a 0.8-fold improvement to about a 1-fold improvement, about a 1-fold improvement to about a 100-fold improvement, about a 1-fold improvement to about a 50-fold improvement, about a 1-fold improvement to about a 30-fold improvement, about a 1-fold improvement to about a 20-fold improvement, about a 1-fold improvement to about a 15-fold improvement, about a 1-fold improvement to about a 10-fold improvement, about a 1-fold improvement to about a 8-fold improvement, about a 1-fold improvement to about a 6-fold improvement, about a 1-fold improvement to about a 4-fold improvement, about a 1-fold improvement to about a 2-fold improvement, about a 2-fold improvement to about a 100-fold improvement, about a 2-fold improvement to about a 50-fold improvement, about a 2-fold improvement to about a 30-fold improvement, about a 2-fold improvement to about a 20-fold improvement, about a 2-fold improvement to about a 15-fold improvement, about a 2-fold improvement to about a 10-fold improvement, about a 2-fold improvement to about a 8-fold improvement, about a 2-fold improvement to about a 6-fold improvement, about a 2-fold improvement to about a 4-fold improvement, about a 4-fold improvement to about a 100-fold improvement, about a 4-fold improvement to about a 50-fold improvement, about a 4-fold improvement to about a 30-fold improvement, about a 4-fold improvement to about a 20-fold improvement, about a 4-fold improvement to about a 15-fold improvement, about a 4-fold improvement to about a 10-fold improvement, about a 4-fold improvement to about a 8-fold improvement, about a 4-fold improvement to about a 6-fold improvement, about a 6-fold improvement to about a 100-fold improvement, about a 6-fold improvement to about a 50-fold improvement, about a 6-fold improvement to about a 30-fold improvement, about a 6-fold improvement to about a 20-fold improvement, about a 6-fold improvement to about a 15-fold improvement, about a 6-fold improvement to about a 10-fold improvement, about a 6-fold improvement to about a 8-fold improvement, about a 8-fold improvement to about a 100-fold improvement, about a 8-fold improvement to about a 50-fold improvement, about a 8-fold improvement to about a 30-fold improvement, about a 8-fold improvement to about a 20-fold improvement, about a 8-fold improvement to about a 15-fold improvement, about a 8-fold improvement to about a 10-fold improvement, about a 10-fold improvement to about a 100-fold improvement, about a 10-fold improvement to about a 50-fold improvement, about a 10-fold improvement to about a 30-fold improvement, about a 10-fold improvement to about a 20-fold improvement, about a 10-fold improvement to about a 15-fold improvement, about a 15-fold improvement to about a 100-fold improvement, about a 15-fold improvement to about a 50-fold improvement, about a 15-fold improvement to about a 30-fold improvement, about a 15-fold improvement to about a 20-fold improvement, about a 20-fold improvement to about a 100-fold improvement, about a 20-fold improvement to about a 50-fold improvement, about a 20-fold improvement to about a 30-fold improvement, about a 30-fold improvement to about a 100-fold improvement, about a 30-fold improvement to about a 50-fold improvement, or about a 50-fold improvement to about 100-fold improvement, in the signal to noise ratio as compared to a similar method performed without the use of a diffusion-restricted nuclease.

Some embodiments of any of the methods described herein can provide for at least a 0.1-fold improvement, at least a 0.5-fold improvement, at least a 1-fold improvement, at least a 1.5-fold improvement, at least a 2-fold improvement, at least a 2.5-fold improvement, at least a 3-fold improvement, at least a 3.5-fold improvement, at least a 4-fold improvement, at least a 4.5-fold improvement, at least a 5-fold improvement, at least a 5.5-fold improvement, at least a 6-fold improvement, at least a 6.5-fold improvement, at least a 7-fold improvement, at least a 7.5-fold improvement, at least a 8-fold improvement, at least a 8.5-fold improvement, at least a 9-fold improvement, at least a 9.5-fold improvement, at least 10-fold improvement, at least a 15-fold improvement, at least a 20-fold improvement, at least 30-fold improvement, at least 50-fold improvement, at least 100-fold improvement in the sequencing yield per spot as compared to a similar method performed without the use of a diffusion-restricted nuclease.

Some embodiments of any of the methods described herein can provide for about a 0.1-fold improvement to about a 100-fold improvement, about a 0.1-fold improvement to about a 50-fold improvement, about a 0.1-fold improvement to about a 30-fold improvement, about a 0.1-fold improvement to about a 20-fold improvement, about a 0.1-fold improvement to about a 15-fold improvement, about a 0.1-fold improvement to about a 10-fold improvement, about a 0.1-fold improvement to about a 8-fold improvement, about a 0.1-fold improvement to about a 6-fold improvement, about a 0.1-fold improvement to about a 4-fold improvement, about a 0.1-fold improvement to about a 2-fold improvement, about a 0.1-fold improvement to about a 1-fold improvement, about a 0.1-fold improvement to about a 0.5-fold improvement, about a 0.1-fold improvement to about a 0.2-fold improvement, about a 0.2-fold improvement to about a 100-fold improvement, about a 0.2-fold improvement to about a 50-fold improvement, about a 0.2-fold improvement to about a 30-fold improvement, about a 0.2-fold improvement to about a 20-fold improvement, about a 0.2-fold improvement to about a 15-fold improvement, about a 0.2-fold improvement to about a 10-fold improvement, about a 0.2-fold improvement to about a 8-fold improvement, about a 0.2-fold improvement to about a 6-fold improvement, about a 0.2-fold improvement to about a 4-fold improvement, about a 0.2-fold improvement to about a 2-fold improvement, about a 0.2-fold improvement to about a 1-fold improvement, about a 0.2-fold improvement to about a 0.5-fold improvement, about a 0.5-fold improvement to about a 100-fold improvement, about a 0.5-fold improvement to about a 50-fold improvement, about a 0.5-fold improvement to about a 30-fold improvement, about a 0.5-fold improvement to about a 20-fold improvement, about a 0.5-fold improvement to about a 15-fold improvement, about a 0.5-fold improvement to about a 10-fold improvement, about a 0.5-fold improvement to about a 8-fold improvement, about a 0.5-fold improvement to about a 6-fold improvement, about a 0.5-fold improvement to about a 4-fold improvement, about a 0.5-fold improvement to about a 2-fold improvement, about a 0.5-fold improvement to about a 1-fold improvement, about a 1-fold improvement to about a 100-fold improvement, about a 1-fold improvement to about a 50-fold improvement, about a 1-fold improvement to about a 30-fold improvement, about a 1-fold improvement to about a 20-fold improvement, about a 1-fold improvement to about a 15-fold improvement, about a 1-fold improvement to about a 10-fold improvement, about a 1-fold improvement to about a 8-fold improvement, about a 1-fold improvement to about a 6-fold improvement, about a 1-fold improvement to about a 4-fold improvement, about a 1-fold improvement to about a 2-fold improvement, about a 2-fold improvement to about a 100-fold improvement, about a 2-fold improvement to about a 50-fold improvement, about a 2-fold improvement to about a 30-fold improvement, about a 2-fold improvement to about a 20-fold improvement, about a 2-fold improvement to about a 15-fold improvement, about a 2-fold improvement to about a 10-fold improvement, about a 2-fold improvement to about a 8-fold improvement, about a 2-fold improvement to about a 6-fold improvement, about a 2-fold improvement to about a 4-fold improvement, about a 4-fold improvement to about a 100-fold improvement, about a 4-fold improvement to about a 50-fold improvement, about a 4-fold improvement to about a 30-fold improvement, about a 4-fold improvement to about a 20-fold improvement, about a 4-fold improvement to about a 15-fold improvement, about a 4-fold improvement to about a 10-fold improvement, about a 4-fold improvement to about a 8-fold improvement, about a 4-fold improvement to about a 6-fold improvement, about a 6-fold improvement to about a 100-fold improvement, about a 6-fold improvement to about a 50-fold improvement, about a 6-fold improvement to about a 30-fold improvement, about a 6-fold improvement to about a 20-fold improvement, about a 6-fold improvement to about a 15-fold improvement, about a 6-fold improvement to about a 10-fold improvement, about a 6-fold improvement to about a 8-fold improvement, about a 8-fold improvement to about a 100-fold improvement, about a 8-fold improvement to about a 50-fold improvement, about a 8-fold improvement to about a 30-fold improvement, about a 8-fold improvement to about a 20-fold improvement, about a 8-fold improvement to about a 15-fold improvement, about a 8-fold improvement to about a 10-fold improvement, about a 10-fold improvement to about a 100-fold improvement, about a 10-fold improvement to about a 50-fold improvement, about a 10-fold improvement to about a 30-fold improvement, about a 10-fold improvement to about a 20-fold improvement, about a 10-fold improvement to about a 15-fold improvement, about a 15-fold improvement to about a 100-fold improvement, about a 15-fold improvement to about a 50-fold improvement, about a 15-fold improvement to about a 30-fold improvement, about a 15-fold improvement to about a 20-fold improvement, about a 20-fold improvement to about a 100-fold improvement, about a 20-fold improvement to about a 50-fold improvement, about a 20-fold improvement to about a 30-fold improvement, about a 30-fold improvement to about a 100-fold improvement, about a 30-fold improvement to about a 50-fold improvement, or about a 50-fold improvement to about a 100-fold improvement, in the sequencing yield per spot as compared to a similar method performed without the use of a diffusion-restricted nuclease Additional non-limiting aspects of these methods are described herein and can be used in any combination.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363 (6434): 1463-1467, 2019; Lee et al., Nat. Protoc. 10 (3): 442-458, 2015; Trejo et al., PLOS ONE 14 (2):e0212031, 2019; Chen et al., Science 348 (6233): aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available on the 10× Genomics Support Documentation website, and can be used herein in any combination. Further non-limiting aspects of spatial analysis methodologies and compositions are described herein.

Some general terminology that may be used in this disclosure can be found in Section (I) (b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I) (c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I) (d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I) (d) (ii) (13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain).

A "spatial barcode" is a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate.

The "capture domain" can be an oligonucleotide, a polypeptide, a small molecule, or any combination thereof, that binds specifically to a desired analyte. In some embodiments, a capture domain can be used to capture or detect a desired analyte.

In some embodiments, a capture probe can include a cleavage domain and/or a functional domain (e.g., a primer-binding site, such as for next-generation sequencing (NGS)). See, e.g., Section (II) (b) (e.g., subsections (i)-(vi)) of WO 2020/176788 and/or U.S. Patent Application Publication No. 2020/0277663. Generation of capture probes can be achieved by any appropriate method, including those described in Section (II) (d) (ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent.

The term "analyte binding moiety" refers to a molecule or moiety capable of binding to a macromolecular constituent (e.g., an analyte, e.g., a biological analyte). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific target molecule, e.g., an analyte). The analyte binding moiety can include an antibody or antibody fragment (e.g., an antigen-binding fragment) that binds to a specific analyte (e.g., a polypeptide).

Additional description of analyte capture agents can be found in Section (II) (b) (ix) of WO 2020/176788 and/or Section (II) (b) (viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II) (b) (vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II) (a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II) (g) of WO 2020/176788 and/or U.S. Patent Application Publication No. 2020/0277663. Some quality control measures are described in Section (II) (h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II) (c) of WO 2020/176788 and/or U.S. Patent Application Publication No. 2020/0277663. Exemplary features and geometric attributes of an array can be found in Sections (II) (d) (i), (II) (d) (iii), and (II) (d) (iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II) (e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45 (14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II) (e) (ii) and/or (V) of WO 2020/176788 and/or U.S. Patent Application Publication No. 2020/0277663, or any of one or more of the devices or methods described in Sections *Control Slide for Imaging, Methods of Using Control Slides and Substrates for, Systems of Using Control Slides and Substrates for Imaging, and/or Sample and Array Alignment Devices and Methods, Informational labels* of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein. In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the *Substrate Attributes* Section, *Control Slide for Imaging* Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

I. First and Second Areas

Some embodiments of any of the methods described herein include disposing a biological sample (e.g., a non-permeabilized biological sample) onto an array (e.g., any of the exemplary arrays described herein), where the array has a first area covered by the non-permeabilized biological sample and a second area not covered by the non-permeabilized biological sample.

The first area can represent a portion of the array that is covered by the biological sample, e.g., at least 1%, at least 2%, at least 4%, at least 6%, at least 8%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, of the total area of the array covered by the biological sample.

In some examples, the first area can represent a portion of the array that is covered by the biological sample, e.g., about 1% to about 100%, about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 35%, about 1% to about 20%, about 1% to about 15%, about 1% to about 10%, about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%, of the total area of the array covered by the biological sample.

The second area can represent a portion of the array that is not covered by the biological sample, e.g., at least 1%, at least 2%, at least 4%, at least 6%, at least 8%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, of the total area of the array not covered by the biological sample. In some examples, the second area can represent a portion of the array that is not covered by the biological sample, e.g., about 1% to about 100%, about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 35%, about 1% to about 20%, about 1% to about 15%, about 1% to about 10%, about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%, of the total area of the array not covered by the biological sample.

II. Diffusion-Restricted Nucleases

In some embodiments, the nuclease present is a diffusion-restricted, an enzyme capable of cleaving the phosphodiester bonds between nucleotides of nucleic acids (e.g. RNA and/or DNA). In some embodiments, the nuclease degrades single-strand nucleic acids (e.g., single-stranded DNA and/or single-stranded RNA). In some embodiments, the nuclease degrades double-strand nucleic acids (e.g., double-stranded DNA, double-stranded RNA, or a double-stranded DNA/RNA molecule). In some embodiments, the nuclease is an endonuclease. In some embodiment, the nuclease is an exonuclease. In some embodiments, the nuclease is a deoxyribonuclease (DNAse). In some embodiments, the nuclease is a ribonuclease (RNAse). In some embodiments, the nuclease is a 3' to 5' exonuclease. In some embodiments, the nuclease is a DNAse I (e.g., bovine pancreatic DNAse I). In some embodiments, the nuclease is a DNAse II. In some embodiments, the nuclease is a wild-type DNAse. In some embodiments, the nuclease comprises an amino acid sequence that is at least 70%, 75%, 80%, 85%, 90%, 95%, 99%, or 100% identical to the amino acid sequence of a wild-type DNase. In some embodiments, the nuclease comprises at least 1, 2, 3, 4, 5, 6, 7, 8, 9, 10, 11, 12, 13, 14, 15, 16, 17, 18, 19, 20, about 30, about 40, or about 50 amino acid substitutions compared to the amino acid sequence of a wild-type DNAse. In some embodiments, the nuclease is a recombinant nuclease. In some embodiments, the nuclease is expressed in a host bacterial strain (e.g., *E. coli*) or a host cell (e.g., insect cell). In some embodiments, the nuclease comprises additional amino acid sequences that can facilitate recombinant nuclease expression and purification (e.g., poly-histidine tag or GST tag). In some embodiments, the recombinant nuclease is encoded by a nucleic acid sequence that is at least 70%, 75%, 80%, 85%, 90%, 95%, 99%, or 100% identical to the nucleic acid sequence encoding a wild-type DNase. In some embodiments, the recombinant nuclease is encoded by a nucleic acid sequence that has at least 1, 2, 3, 4, 5, 6, 7, 8, 9, 10, 11, 12, 13, 14, 15, 16, 17, 18, 19, 20, about 30, about 40, about 50, about 60, about 70, about 80, about 90, or about 100 mutations (e.g., point mutations) compared to the nucleic acid sequence encoding a wild-type DNAse.

In some embodiments, the diffusion-restricted nuclease is covalently conjugated or non-covalently attached to a bead. For example, a bead not having a capture probe attached but having a similar shape, dimension, material, size, coating, appearance, and/or physical properties, as compared to any of the other beads described herein.

In some embodiments, the diffusion-restricted nuclease is covalently conjugated or non-covalently attached to a particle. In some embodiments, the particle can be rigid. In some embodiments, the particle can be flexible and/or compressible. A particle can generally be of any suitable shape. Examples of particle shapes include, but are not limited to, spherical, non-spherical, oval, oblong, amorphous, circular, cylindrical, cuboidal, hexagonal, and variations thereof. Particles can be of uniform size or heterogeneous size.

In some embodiments, the particle can have a diameter or maximum dimension no larger than 100 µm (e.g., no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm).

In some embodiments, a plurality of particles has an average diameter no larger than 100 µm. In some embodiments, a plurality of particles has an average diameter or maximum dimension no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm.

In some embodiments, the volume of the particle can be at least about 1 µm$^3$, e.g., at least 1 µm$^3$, 2 µm$^3$, 3 µm$^3$, 4 µm$^3$, 5 µm$^3$, 6 µm$^3$, 7 µm$^3$, 8 µm$^3$, 9 µm$^3$, 10 µm$^3$, 12 µm$^3$, 14 µm$^3$, 16 µm$^3$, 18 µm$^3$, 20 µm$^3$, 25 µm$^3$, 30 µm$^3$, 35 µm$^3$, 40 µm$^3$, 45 µm$^3$, 50 µm$^3$, 55 µm$^3$, 60 µm$^3$, 65 µm$^3$, 70 µm$^3$, 75 µm$^3$, 80 µm$^3$, 85 µm$^3$, 90 µm$^3$, 95 µm$^3$, 100 µm$^3$, 125 µm$^3$, 150 µm$^3$, 175 µm$^3$, 200 µm$^3$, 250 µm$^3$, 300 µm$^3$, 350 µm$^3$, 400 µm$^3$, 450 µm$^3$, µm$^3$, 500 µm$^3$, 550 µm$^3$, 600 µm$^3$, 650 µm$^3$, 700 µm$^3$, 750 µm$^3$, 800 µm$^3$, 850 µm$^3$, 900 µm$^3$, 950 µm$^3$, 1000 µm$^3$, 1200 µm$^3$, 1400 µm$^3$, 1600 µm$^3$, 1800 µm$^3$, 2000 µm$^3$, 2200 µm$^3$, 2400 µm$^3$, 2600 µm$^3$, 2800 µm$^3$, 3000 µm$^3$, or greater.

In some embodiments, the particle can have a volume of between about 1 µm$^3$ and 100 µm$^3$, such as between about 1 µm$^3$ and 10 µm$^3$, between about 10 µm$^3$ and 50 µm$^3$, or between about 50 µm$^3$ and 100 µm$^3$. In some embodiments, the particle can include a volume of between about 100 µm$^3$ and 1000 µm$^3$, such as between about 100 µm$^3$ and 500 µm$^3$ or between about 500 µm$^3$ and 1000 µm$^3$. In some embodiments, the particle can include a volume between about 1000 µm$^3$ and 3000 µm$^3$, such as between about 1000 µm$^3$ and 2000 µm$^3$ or between about 2000 µm$^3$ and 3000 µm$^3$. In some embodiments, the particle can include a volume between about 1 µm³ and 3000 µm³, such as between about 1 µm³ and 2000 µm³, between about 1 µm³ and 1000 µm³, between about 1 µm³ and 500 µm³, or between about 1 µm³ and 250 µm³.

The particle can include two or more cross-section(s) that can be the same or different. In some embodiments, the particle can have a first cross-section that is different from a second cross-section. The particle can have a first cross-section that is at least about 0.0001 micrometer, at least 0.001 micrometer, at least 0.01 micrometer, at least 0.1 micrometer, or at least 1 micrometer. In some embodiments, the particle can include a cross-section (e.g., a first cross-section) of at least about 1 micrometer (µm), at least about 2 µm, at least about 3 µm, at least about 4 µm, at least about 5 µm, at least about 6 µm, at least about 7 µm, at least about 8 µm, at least about 9 µm, at least about 10 µm, at least about 11 µm, at least about 12 µm, at least about 13 µm, at least about 14 µm, at least about 15 µm, at least about 16 µm, at least about 17 µm, at least about 18 µm, at least about 19 µm, at least about 20 µm, or at least about 25 µm. In some embodiments, the particle can include a cross-section (e.g., a first cross-section) of about 0.01 µm to about 25 µm, about 0.01 µm to about 20 µm, about 0.01 µm to about 18 µm, about 0.01 µm to about 16 µm, about 0.01 µm to about 14 µm, about 0.01 µm to about 12 µm, about 0.01 µm to about 10 µm, about 0.01 µm to about 8 µm, about 0.01 µm to about 6 µm, about 0.01 µm to about 4 µm, about 0.01 µm to about 2 µm, about 0.01 µm to about 1 µm, about 0.01 µm to about 0.5 µm, about 0.01 µm to about 0.1 µm, about 0.01 µm to about 0.05 µm, about 0.05 µm and 25 µm, about 0.05 µm to about 20 µm, about 0.05 µm to about 18 µm, about 0.05 µm to about 16 µm, about 0.05 µm to about 14 µm, about 0.05 µm to about 12 µm, about 0.05 µm to about 10 µm, about 0.05 µm to about 8 µm, about 0.05 µm to about 6 µm, about 0.05 µm to about 4 µm, about 0.05 µm to about 2 µm, about 0.05 µm to about 1 µm, about 0.05 µm to about 0.5 µm, about 0.05 µm to about 0.1 µm, about 0.1 µm and 25 µm, about 0.1 µm to about 20 µm, about 0.1 µm to about 18 µm, about 0.1 µm to about 16 µm, about 0.1 µm to about 14 µm, about 0.1 µm to about 12 µm, about 0.1 µm to about 10 µm, about 0.1 µm to about 8 µm, about 0.1 µm to about 6 µm, about 0.1 µm to about 4 µm, about 0.1 µm to about 2 µm, about 0.1 µm to about 1 µm, about 0.1 µm to about 0.5 µm, about 0.5 µm and 25 µm, about 0.5 µm to about 20 µm, about 0.5 µm to about 18 µm, about 0.5 µm to about 16 µm, about 0.5 µm to about 14 µm, about 0.5 µm to about 12 µm, about 0.5 µm to about 10 µm, about 0.5 µm to about 8 µm, about 0.5 µm to about 6 µm, about 0.5 µm to about 4 µm, about 0.5 µm to about 2 µm, about 0.5 µm to about 1 µm, about 1 µm and 25 µm, about 1 µm to about 20 µm, about 1 µm to about 18 µm, about 1 µm to about 16 µm, about 1 µm to about 14 µm, about 1 µm to about 12 µm, about 1 µm to about 10 µm, about 1 µm to about 8 µm, about 1 µm to about 6 µm, about 1 µm to about 4 µm, about 1 µm to about 2 µm, about 2 µm and 25 µm, about 2 µm to about 20 µm, about 2 µm to about 18 µm, about 2 µm to about 16 µm, about 2 µm to about 14 µm, about 2 µm to about 12 µm, about 2 µm to about 10 µm, about 2 µm to about 8 µm, about 2 µm to about 6 µm, about 2 µm to about 4 µm, about 4 µm and 25 µm, about 4 µm to about 20 µm, about 4 µm to about 18 µm, about 4 µm to about 16 µm, about 4 µm to about 14 µm, about 4 µm to about 12 µm, about 4 µm to about 10 µm, about 4 µm to about 8 µm, about 4 µm to about 6 µm, about 6 µm and 25 µm, about 6 µm to about 20 µm, about 6 µm to about 18 µm, about 6 µm to about 16 µm, about 6 µm to about 14 µm, about 6 µm to about 12 µm, about 6 µm to about 10 µm, about 6 µm to about 8 µm, about 8 µm and 25 µm, about 8 µm to about 20 µm, about 8 µm to about 18 µm, about 8 µm to about 16 µm, about 8 µm to about 14 µm, about 8 µm to about 12 µm, about 8 µm to about 10 µm, about 10 µm and 25 µm, about 10 µm to about 20 µm, about 10 µm to about 18 µm, about 10 µm to about 16 µm, about 10 µm to about 14 µm, about 10 µm to about 12 µm, about 12 µm and 25 µm, about 12 µm to about 20 µm, about 12 µm to about 18 µm, about 12 µm to about 16 µm, about 12 µm to about 14 µm, about 14 µm and 25 µm, about 14 µm to about 20 µm, about 14 µm to about 18 µm, about 14 µm to about 16 µm, about 16 µm and 25 µm, about 16 µm to about 20 µm, about 16 µm to about 18 µm, about 18 µm and 25 µm, about 18 µm to about 20 µm, or about 20 µm to about 25 µm.

For example, the particle can include a cross-section (e.g., a first cross-section) of about 1 µm to 100 µm. In some embodiments, the particle can have a second cross-section that is at least about 1 µm. For example, the particle can include a second cross-section of at least about 1 µm, at least about 2 µm, at least about 3 µm, at least about 4 µm, at least about 5 µm, at least about 6 µm, at least about 7 µm, at least about 8 µm, at least about 9 µm, at least about 10 µm, at least about 11 µm, at least about 12 µm, at least about 13 µm, at least about 14 µm, at least about 15 µm, at least about 16 µm, at least about 17 µm, at least about 18 µm, at least about 19 µm, at least about 20 µm, at least about 25 µm, at least about 30 µm, at least about 35 µm, at least about 40 µm, at least about 45 µm, at least about 50 µm, at least about 55 µm, at least about 60 µm, at least about 65 µm, at least about 70 µm, at least about 75 µm, at least about 80 µm, at least about 85 µm, at least about 90 µm, at least about 100 µm, at least about 120 µm, at least about 140 µm, at least about 160 µm, at least about 180 µm, at least about 200 µm, at least about 250 µm, at least about 300 µm, at least about 350 µm, at least about 400 µm, at least about 450 µm, or at least about 500 µm. In some embodiments, the particle can include a second cross-section of about 1 µm to about 500 µm, about 1 µm to about 450 µm, about 1 µm to about 400 µm, about 1 µm to about 350 µm, about 1 µm to about 300 µm, about 1 µm to about 250 µm, about 1 µm to about 200 µm, about 1 µm to about 150 µm, about 1 µm to about 100 µm, about 1 µm to about 80 µm, about 1 µm to about 60 µm, about 1 µm to about 40 µm, about 1 µm to about 20 µm, about 1 µm to about 15 µm, about 1 µm to about 10 µm, about 1 µm to about 8 µm, about 1 µm to about 6 µm, about 1 µm to about 4 µm, about 1 µm to about 2 µm, about 2 µm to about 500 µm, about 2 µm to about 450 µm, about 2 µm to about 400 µm, about 2 µm to about 350 µm, about 2 µm to about 300 µm, about 2 µm to about 250 µm, about 2 µm to about 200 µm, about 2 µm to about 150 µm, about 2 µm to about 100 µm, about 2 µm to about 80 µm, about 2 µm to about 60 µm, about 2 µm to about 40 µm, about 2 µm to about 20 µm, about 2 µm to about 15 µm, about 2 µm to about 10 µm, about 2 µm to about 8 µm, about 2 µm to about 6 µm, about 2 µm to about 4 µm, about 4 µm to about 500 µm, about 4 µm to about 450 µm, about 4 µm to about 400 µm, about 4 µm to about 350 µm, about 4 µm to about 300 µm, about 4 µm to about 250 µm, about 4 µm to about 200 µm, about 4 µm to about 150 µm, about 4 µm to about 100 µm, about 4 µm to about 80 µm, about 4 µm to about 60 µm, about 4 µm to about 40 µm, about 4 µm to about 20 µm, about 4 µm to about 15 µm, about 4 µm to about 10 µm, about 4 µm to about 8 µm, about 4 µm to about 6 µm, about 6 µm to about 500 µm, about 6 µm to about 450 µm, about 6 µm to about 400 µm, about 6 µm to about 350 µm, about 6 µm to about 300 µm, about 6 µm to about 250 µm, about 6 µm to about 200 µm, about 6 µm to about 150 µm, about 6 µm to about 100 µm, about 6 µm to about 80 µm, about 6 µm to about 60 µm, about 6 µm to about 40 µm, about 6 µm to about 20 µm, about 6 µm to about 15 µm, about 6 µm to about 10 µm, about 6 µm to about 8 µm, about 8 µm to about 500 µm, about 8 µm to about 450 µm, about 8 µm to about 400 µm, about 8 µm to about 350 µm, about 8 µm to about 300 µm, about 8 µm to about 250 µm, about 8 µm to about 200 µm, about 8 µm to about 150 µm, about 8 µm to about 100 µm, about 8 µm to about 80 µm, about 8 µm to about 60 µm, about 8 µm to about 40 µm, about 8 µm to about 20 µm, about 8 µm to about 15 µm, about 8 µm to about 10 µm, about 10 µm to about 500 µm, about 10 µm to about 450 µm, about 10 µm to about 400 µm, about 10 µm to about 350 µm, about 10 µm to about 300 µm, about 10 µm to about 250 µm, about 10 µm to about 200 µm, about 10 µm to about 150 µm, about 10 µm to about 100 µm, about 10 µm to about 80 µm, about 10 µm to about 60 µm, about 10 µm to about 40 µm, about 10 µm to about 20 µm, about 10 µm to about 15 µm, about 15 µm to about 500 µm, about 15 µm to about 450 µm, about 15 µm to about 400 µm, about 15 µm to about 350 µm, about 15 µm to about 300 µm, about 15 µm to about 250 µm, about 15 µm to about 200 µm, about 15 µm to about 150 µm, about 15 µm to about 100 µm, about 15 µm to about 80 µm, about 15 µm to about 60 µm, about 15 µm to about 40 µm, about 15 µm to about 20 µm, about 20 µm to about 500 µm, about 20 µm to about 450 µm, about 20 µm to about 400 µm, about 20 µm to about 350 µm, about 20 µm to about 300 µm, about 20 µm to about 250 µm, about 20 µm to about 200 µm, about 20 µm to about 150 µm, about 20 µm to about 100 µm, about 20 µm to about 80 µm, about 20 µm to about 60 µm, about 20 µm to about 40 µm, about 40 µm to about 500 µm, about 40 µm to about 450 µm, about 40 µm to about 400 µm, about 40 µm to about 350 µm, about 40 µm to about 300 µm, about 40 µm to about 250 µm, about 40 µm to about 200 µm, about 40 µm to about 150 µm, about 40 µm to about 100 µm, about 40 µm to about 80 µm, about 40 µm to about 60 µm, about 60 µm to about 500 µm, about 60 µm to about 450 µm, about 60 µm to about 400 µm, about 60 µm to about 350 µm, about 60 µm to about 300 µm, about 60 µm to about 250 µm, about 60 µm to about 200 µm, about 60 µm to about 150 µm, about 60 µm to about 100 µm, about 60 µm to about 80 µm, about 80 µm to about 500 µm, about 80 µm to about 450 µm, about 80 µm to about 400 µm, about 80 µm to about 350 µm, about 80 µm to about 300 µm, about 80 µm to about 250 µm, about 80 µm to about 200 µm, about 80 µm to about 150 µm, about 80 µm to about 100 µm, about 100 µm to about 500 µm, about 100 µm to about 450 µm, about 100 µm to about 400 µm, about 100 µm to about 350 µm, about 100 µm to about 300 µm, about 100 µm to about 250 µm, about 100 µm to about 200 µm, about 100 µm to about 150 µm, about 150 µm to about 500 µm, about 150 µm to about 450 µm, about 150 µm to about 400 µm, about 150 µm to about 350 µm, about 150 µm to about 300 µm, about 150 µm to about 250 µm, about 150 µm to about 200 µm, about 200 µm to about 500 µm, about 200 µm to about 450 µm, about 200 µm to about 400 µm, about 200 µm to about 350 µm, about 200 µm to about 300 µm, about 200 µm to about 250 µm, about 250 µm to about 500 µm, about 250 µm to about 450 µm, about 250 µm to about 400 µm, about 250 µm to about 350 µm, about 250 µm to about 300 µm, about 300 µm to about 500 µm, about 300 µm to about 450 µm, about 300 µm to about 400 µm, about 300 µm to about 350 µm, about 350 µm to about 500 µm, about 350 µm to about 450 µm, about 350 µm to about 400 µm, about 400 µm to about 500 µm, about 400 µm to about 450 µm, about 450 µm to about 500 µm.

In some embodiments, particles can be of a nanometer scale (e.g., particles can have a diameter or maximum cross-sectional dimension of about 10 nm to about 900 nm, about 10 nm to about 850 nm, about 10 nm to about 800 nm, about 10 nm to about 750 nm, about 10 nm to about 700 nm, about 10 nm to about 650 nm, about 10 nm to about 600 nm, about 10 nm to about 550 nm, about 10 nm to about 500 nm, about 10 nm to about 450 nm, about 10 nm to about 400 nm, about 10 nm to about 350 nm, about 10 nm to about 300 nm, about 10 nm to about 250 nm, about 10 nm to about 200 nm, about 10 nm to about 150 nm, about 10 nm to about 100 nm, about 10 nm to about 50 nm, about 50 nm to about 900 nm, about 50 nm to about 850 nm, about 50 nm to about 800 nm, about 50 nm to about 750 nm, about 50 nm to about 700 nm, about 50 nm to about 650 nm, about 50 nm to about 600 nm, about 50 nm to about 550 nm, about 50 nm to about 500 nm, about 50 nm to about 450 nm, about 50 nm to about 400 nm, about 50 nm to about 350 nm, about 50 nm to about 300 nm, about 50 nm to about 250 nm, about 50 nm to about 200 nm, about 50 nm to about 150 nm, about 50 nm to about 100 nm, about 100 nm to about 900 nm, about 100 nm to about 850 nm, about 100 nm to about 800 nm, about 100 nm to about 750 nm, about 100 nm to about 700 nm, about 100 nm to about 650 nm, about 100 nm to about 600 nm, about 100 nm to about 550 nm, about 100 nm to about 500 nm, about 100 nm to about 450 nm, about 100 nm to about 400 nm, about 100 nm to about 350 nm, about 100 nm to about 300 nm, about 100 nm to about 250 nm, about 100 nm to about 200 nm, about 100 nm to about 150 nm, about 150 nm to about 900 nm, about 150 nm to about 850 nm, about 150 nm to about 800 nm, about 150 nm to about 750 nm, about 150 nm to about 700 nm, about 150 nm to about 650 nm, about 150 nm to about 600 nm, about 150 nm to about 550 nm, about 150 nm to about 500 nm, about 150 nm to about 450 nm, about 150 nm to about 400 nm, about 150 nm to about 350 nm, about 150 nm to about 300 nm, about 150 nm to about 250 nm, about 150 nm to about 200 nm, about 200 nm to about 900 nm, about 200 nm to about 850 nm, about 200 nm to about 800 nm, about 200 nm to about 750 nm, about 200 nm to about 700 nm, about 200 nm to about 650 nm, about 200 nm to about 600 nm, about 200 nm to about 550 nm, about 200 nm to about 500 nm, about 200 nm to about 450 nm, about 200 nm to about 400 nm, about 200 nm to about 350 nm, about 200 nm to about 300 nm, about 200 nm to about 250 nm, about 250 nm to about 900 nm, about 250 nm to about 850 nm, about 250 nm to about 800 nm, about 250 nm to about 750 nm, about 250 nm to about 700 nm, about 250 nm to about 650 nm, about 250 nm to about 600 nm, about 250 nm to about 550 nm, about 250 nm to about 500 nm, about 250 nm to about 450 nm, about 250 nm to about 400 nm, about 250 nm to about 350 nm, about 250 nm to about 300 nm, about 300 nm to about 900 nm, about 300 nm to about 850 nm, about 300 nm to about 800 nm, about 300 nm to about 750 nm, about 300 nm to about 700 nm, about 300 nm to about 650 nm, about 300 nm to about 600 nm, about 300 nm to about 550 nm, about 300 nm to about 500 nm, about 300 nm to about 450 nm, about 300 nm to about 400 nm, about 300 nm to about 350 nm, about 350 nm to about 900 nm, about 350 nm to about 850 nm, about 350 nm to about 800 nm, about 350 nm to about 750 nm, about 350 nm to about 700 nm, about 350 nm to about 650 nm, about 350 nm to about 600 nm, about 350 nm to about 550 nm, about 350 nm to about 500 nm, about 350 nm to about 450 nm, about 350 nm to about 400 nm, about 400 nm to about 900 nm, about 400 nm to about 850 nm, about 400 nm to about 800 nm, about 400 nm to about 750 nm, about 400 nm to about 700 nm, about 400 nm to about 650 nm, about 400 nm to about 600 nm, about 400 nm to about 550 nm, about 400 nm to about 500 nm, about 400 nm to about 450 nm, about 450 nm to about 900 nm, about 450 nm to about 850 nm, about 450 nm to about 800 nm, about 450 nm to about 750 nm, about 450 nm to about 700 nm, about 450 nm to about 650 nm, about 450 nm to about 600 nm, about 450 nm to about 550 nm, about 450 nm to about 500 nm, about 500 nm to about 900 nm, about 500 nm to about 850 nm, about 500 nm to about 800 nm, about 500 nm to about 750 nm, about 500 nm to about 700 nm, about 500 nm to about 650 nm, about 500 nm to about 600 nm, about 500 nm to about 550 nm, about 550 nm to about 900 nm, about 550 nm to about 850 nm, about 550 nm to about 800 nm, about 550 nm to about 750 nm, about 550 nm to about 700 nm, about 550 nm to about 650 nm, about 550 nm to about 600 nm, about 600 nm to about 900 nm, about 600 nm to about 850 nm, about 600 nm to about 800 nm, about 600 nm to about 750 nm, about 600 nm to about 700 nm, about 600 nm to about 650 nm, about 650 nm to about 900 nm, about 650 nm to about 850 nm, about 650 nm to about 800 nm, about 650 nm to about 750 nm, about 650 nm to about 700 nm, about 700 nm to about 900 nm, about 700 nm to about 850 nm, about 700 nm to about 800 nm, about 700 nm to about 750 nm, about 750 nm to about 900 nm, about 750 nm to about 850 nm, about 750 nm to about 800 nm, about 800 nm to about 900 nm, about 800 nm to about 850 nm, or about 850 nm to about 900 nm.

In some embodiments, a particle has a diameter or volume that is about the diameter of a single cell (e.g., a single cell under evaluation).

In some embodiments, the diffusion-restricted nuclease is covalently conjugated to a polymer. The polymer can be a natural polymer, a synthetic polymer, or a combination of both natural and synthetic polymers. Examples of natural polymers include, without limitation, proteins, sugars such as deoxyribonucleic acid, rubber, cellulose, starch (e.g., amylose and amylopectin), polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include, without limitation, acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride), and/or combinations (e.g., co-polymers) thereof.

In some embodiments, the polymer can have an average molecular weight of at least about 100 Da (dalton), at least about 200 Da, at least about 300 Da, at least about 400 Da, at least about 500 Da, at least about 600 Da, at least about 700 Da, at least about 800 Da, at least about 900 Da, at least about 1 kDa, at least about 2 kDa, at least about 3 kDa, at least about 4 kDa, at least about 5 kDa, at least about 6 kDa, at least about 7 kDa, at least about 8 kDa, at least about 9 kDa, at least about 10 kDa, at least about 20 kDa, at least about 50 kDa, or at least about 100 kDa. In some embodiments, the polymer can have a molecular weight about 100 Da to about 500 Da, about 500 Da to about 1 kDa, about 1 kDa to about 5 kDa, about 5 kDa to about 20 kDa, about 20 kDa to about 100 kDa.

In some embodiments, the polymer can have a hydrodynamic radius no larger than 100 µm (e.g., no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9µ, 8µ, 7 µm, 6µ, 5µ, 4µ, 3 µm, 2µ, or 1µ m).

In some embodiments, the diffusion-restricted nuclease is conjugated to a bead, a particle, or a polymer through non-covalent interactions, e.g., electrostatic interactions, hydrogen bonds, Van der Waals interactions, hydrophobic interactions, ion-induced dipole interactions, dipole-induced dipole interactions, or any combination thereof.

III. Contacting the Second Area of the Array with a Solution Comprising a Diffusion-Restricted Nuclease In some embodiments, the solution comprising a diffusion-restricted nuclease is added automatically (e.g., by a robot) or manually (e.g., by pipetting). In some embodiments, the solution comprising a diffusion-restricted nuclease is added dropwise by a pipette. In some embodiments, the solution comprising a diffusion-restricted nuclease is added to contact all or a portion of the second area of the array. In some embodiments, the solution comprising a diffusion-restricted nuclease is added to all or a portion of a surface of the non-permeabilized biological sample that is not facing or contacting the array.

In some embodiments, the solution is added vertically above the second area of the array. In some embodiments, the solution is present in liquid form, such that the second area is covered by the solution. In some alternative embodiments, the diffusion-restricted nuclease is contacted to the second area in a gel form or a semifluidic form.

In some embodiments, the concentration of the diffusion-restricted nuclease in the solution is at least about 0.0001 mg/mL, at least about 0.001 mg/mL, at least about 0.01 mg/mL, at least about 0.02 mg/mL, at least about 0.03 mg/mL, at least about 0.04 mg/mL, at least about 0.05 mg/mL, at least about 0.06 mg/mL, at least about 0.07 mg/mL, at least about 0.08 mg/mL, at least about 0.09 mg/mL, at least about 0.1 mg/mL, at least about 0.2 mg/mL, at least about 0.3 mg/mL, at least about 0.4 mg/mL, at least about 0.5 mg/mL, at least about 0.6 mg/mL, at least about 0.7 mg/mL, at least about 0.8 mg/mL, at least about 0.9 mg/mL, at least about 1 mg/mL, at least about 2 mg/mL, at least about 3 mg/mL, at least about 4 mg/mL, at least about 5 mg/mL, at least about 6 mg/mL, at least about 7 mg/mL, at least about 8 mg/mL, at least about 9 mg/mL, at least about 10 mg/mL, at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, at least about 100 mg/mL, at least about 200 mg/mL, at least about 500 mg/maL, at least about 800 mg/mL, or at least about 1000 mg/mL.

In some embodiments, the concentration of the diffusion-restricted nuclease in the solution is at least about 0.001 units/mL, at least about 0.01 units/mL, at least about 0.02 units/mL, at least about 0.03 units/mL, at least about 0.04 units/mL, at least about 0.05 units/mL, at least about 0.06 units/mL, at least about 0.07 units/mL, at least about 0.08 units/mL, at least about 0.09 units/mL, at least about 0.1 units/mL, at least about 0.2 units/mL, at least about 0.3 units/mL, at least about 0.4 units/mL, at least about 0.5 units/mL, at least about 0.6 units/mL, at least about 0.7 units/mL, at least about 0.8 units/mL, at least about 0.9 units/mL, at least about 1 unit/mL, at least about 2 units/mL, at least about 3 units/mL, at least about 4 units/mL, at least about 5 units/mL, at least about 6 units/mL, at least about 7 units/mL, at least about 8 units/mL, at least about 9 units/mL, at least about 10 units/mL, at least about 20 units/mL, at least about 30 units/mL, at least about 40 units/mL, at least about 50 units/mL, at least about 60 units/mL, at least about 70 units/mL, at least about 80 units/mL, at least about 90 units/mL, or at least about 100 units/mL.

In some embodiments, the second area of the array can be contacted by the solution for at least about 5 minutes, at least about 10 minutes, at least about 15 minutes, at least about 20 minutes, at least about 25 minutes, at least about 30 minutes, at least about 40 minutes, at least about 50 minutes, or at least about 1 hour, or greater at a temperature of about 4° C., about 10° C., about 20° C., about 25° C., about 30° C., about 32° C., about 34° C., about 35° C., about 36° C., about 37° C., about 38° C., about 39° C., about 40° C., about 45° C., or about 50° C.

In some embodiments, the second area of the array can be contacted by the solution for about 5 minutes to about 1 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour, at a temperature of about 4° C. to about 35° C., about 4° C. to about 30° C., about 4° C. to about 25° C., about 4° C. to about 20° C., about 4° C. to about 15° C., about 4° C. to about 10° C., about 10° C. to about 35° C., about 10° C. to about 30° C., about 10° C. to about 25° C., about 10° C. to about 20° C., about 10° C. to about 15° C., about 15° C. to about 35° C., about 15° C. to about 30° C., about 15° C. to about 25° C., about 15° C. to about 20° C., about 20° C. to about 35° C., about 20° C. to about 30° C., about 20° C. to about 25° C., about 25° C. to about 35° C., about 25° C. to about 30° C., or about 30° C. to about 35° C.

IV. Removing the Diffusion-Restricted Nuclease from the Second Area of the Array In some embodiments, the solution comprising a diffusion-restricted nuclease is removed by pipetting. In some embodiments, the diffusion-restricted nuclease is removed by wicking (e.g., by an absorption paper). In some embodiments, the diffusion-restricted nuclease is removed by washing (e.g., using a wash buffer). In some embodiments, the wash buffer can be added to contact the second area of the array then removed by pipetting, wicking, or other methods known in the art. In some embodiments, a combination of removing methods can be used. In some embodiments, contacting and removing steps can be repeated (e.g., at least 2 times, 3 times, 4 times, or greater). In some embodiments, a drying step can be performed after washing (e.g., air dry).

In some embodiments, the wash buffer is added automatically (e.g., by a robot) or manually (e.g., by pipetting). In some embodiments, the wash buffer is added vertically above the second area of the array. In some embodiments, the wash buffer is added dropwise by a pipette. In some embodiments, the wash buffer is added to contact all or a portion of the second area of the array. In some embodiments, the wash buffer is added to all or a portion of a surface of the non-permeabilized biological sample that is not facing or contacting the array.

In some embodiments, the wash buffer comprises a nuclease inhibitor so as to stop the diffusion-restricted nuclease from functioning. In some embodiments, the washing buffer is 1× TE buffer, 1× TAE buffer, 1× TBE buffer, or PBS. In some embodiments, the wash buffer contains a buffer (e.g., Tris, MOPS, HEPES, MES, or any other buffer known in the art), chelating agents (e.g., ethylenediaminetetraacetic acid (EDTA)) and/or metal ions (e.g., $Mg^{2+}$). In some embodiments, the wash buffer can have a pH that is about 5.0, about 5.5, about 6.0, about 6.5, about 7.0, about 7.5, about 8.0, about 8.5, about 9.0, about 9.5, or about 10.0, or about 5.0 to 5.5, about 5.5 to 6.0, about 6.0 to 6.5, about 6.5 to 7.0, about 7.0 to 7.5, about 7.5 to 8.0, about 8.0 to 8.5, about 8.5 to 9.0, about 9.0 to 9.5, or about 9.5 to 10.0.

In some embodiments, the second area of the array is contacted by the wash buffer for about 5 seconds to about 1 hour, about 5 seconds to about 50 minutes, about 5 seconds to about 40 minutes, about 5 seconds to about 30 minutes, about 5 seconds to about 20 minutes, about 5 seconds to about 10 minutes, about 5 seconds to about 5 minutes, about 5 seconds to about 1 minute, about 5 seconds to about 30 seconds, about 5 seconds to about 10 seconds, about 10 seconds to about 1 hour, about 10 seconds to about 50 minutes, about 10 seconds to about 40 minutes, about 10 seconds to about 30 minutes, about 10 seconds to about 20 minutes, about 10 seconds to about 10 minutes, about 10 seconds to about 5 minutes, about 10 seconds to about 1 minute, about 10 seconds to about 30 seconds, about 30 seconds to about 1 hour, about 30 seconds to about 50 minutes, about 30 seconds to about 40 minutes, about 30 seconds to about 30 minutes, about 30 seconds to about 20 minutes, about 30 seconds to about 10 minutes, about 30 seconds to about 5 minutes, about 30 seconds to about 1 minute, about 1 minute to about 1 hour, about 1 minute to about 50 minutes, about 1 minute to about 40 minutes, about 1 minute to about 30 minutes, about 1 minute to about 20 minutes, about 1 minute to about 10 minutes, about 1 minute to about 5 minutes, about 5 minutes to about 1 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour at a temperature of about 4° C. to about 35° C., about 4° C. to about 30° C., about 4° C. to about 25° C., about 4° C. to about 20° C., about 4° C. to about 15° C., about 4° C. to about 10° C., about 10° C. to about 35° C. to about 10° C. to about 30° C., about 10° C. to about 25° C., about 10° C. to about 20° C., about 10° C. to about 15° C., about 15° C. to about 35° C., about 15° C. to about 30° C., about 15° C. to about 25° C., about 15° C. to about 20° C., about 20° C. to about 35° C., about 20° C. to about 30° C., about 20° to about 25° C., about 25° C. to about 35° C., about 25° C. to about 30° C., or about 30° C. to about 35° C.

In some embodiments, the second area of the array can be contacted by the wash buffer for at least about 1 second, at least about 5 seconds, at least about 10 seconds, at least about 15 seconds, at least about 20 seconds, at least about 30 seconds, at least about 45 seconds, at least about 1 minutes, at least about 5 minutes, at least about 10 minutes, at least about 15 minutes, at least about 20 minutes, at least about 25 minutes, at least about 30 minutes, at least about 40 minutes, at least about 50 minutes, at least about 1 hour, at a temperature of about 4° C., about 10° C., about 20° C., about 25° C., about 30° C., about 32° C., about 34° C., about 35° C., about 36° C., about 37° C., about 38° C., about 39° C., about 40° C., about 45° C. or about 50° C.

In some embodiments, the solution comprising the diffusion-restricted nuclease contains a gel precursor material (e.g., polyacrylamide) and the diffusion-restricted nuclease is removed by first adding a solution comprising a cross-linking agent (e.g., APS/TEMED) to polymerize or gel the gel precursor material, followed by separating the solution present as a gel from the second area of the array.

In some embodiments, the solution comprising the diffusion-restricted nuclease is present as a gel, and the solution can be removed by separating the gel from the second area of the array.

In some embodiments, the solution comprising the diffusion-restricted nuclease is removed by reducing the temperature of the solution to no more than about 0° C., no more than about −5° C., no more than about −10° C., no more than about −20° C., no more than about −50° C., no more than about −80° C. (e.g., lower than the melting point of the solution), followed by separating the solution in solid form from the second area of the array.

In some embodiments, the diffusion-restricted nuclease is linked to a magnetic bead (or a magnetic particle, or other magnetic substance thereof) and the diffusion-restricted nuclease can be removed by applying a magnetic field.

V. Methods for Determining a Location of a Target Nucleic Acid

Provided herein are methods for determining a location of a target nucleic acid in a biological sample disposed onto an array (e.g., any of the arrays described herein), where the array has a first area covered by the biological sample (e.g., any of the first areas described herein) and a second area not covered by the biological sample (e.g., any of the second areas described herein); where the array comprises a plurality of capture probes (e.g., any of the capture probes described herein), where a capture probe of the plurality of capture probes comprises a spatial barcode (e.g., any of the spatial barcodes described herein) and a capture domain (e.g., any of the capture domains as described herein), where the methods include: (a) contacting the second area of the array with a solution comprising a diffusion-restricted nuclease (e.g., any of the diffusion-restricted nucleases described herein); (b) removing the diffusion-restricted nuclease from the second area of the array (e.g., using any of the methods for removing the diffusion-restricted nucleases described herein); (c) permeabilizing the biological sample, such that the capture domain binds to the target nucleic acid (e.g., using any of the methods for permeabilizing a biological sample described herein); and (d) determining (i) all or a portion of the sequence of the spatial barcode, or a complement thereof, and (ii) all or a portion of the sequence of the target nucleic acid, or a complement thereof, and using the sequences of (i) and (ii) to determine the location of the target nucleic acid in the biological sample.

Non-limiting examples of a target nucleic acid include DNA analytes such as genomic DNA, methylated DNA, specific methylated DNA sequences, fragmented DNA, mitochondrial DNA, in situ synthesized PCR products, and RNA/DNA hybrids.

Non-limiting examples of the target nucleic acid also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments, the target nucleic acid can include at least 1, at least 2, at least 3, at least 4, at least 5, at least 6, at least 7, at least 8, at least 9, or at least 10 disease-causing mutations (e.g., cancer-causing mutations). In some embodiments, the target nucleic acid includes polymorphism, gene amplification, or chromosomal translocation.

In some embodiments, the biological sample as described herein can be stained or imaged by techniques known in the art. In some embodiments, the staining includes optical labels as described herein, including, but not limited to, fluorescent, radioactive, chemiluminescent, calorimetric, or colorimetric detectable labels. In some embodiments, the staining includes a fluorescent antibody directed to a target analyte (e.g., cell surface or intracellular proteins) in the biological sample. In some embodiments, the staining includes an immunohistochemistry stain directed to a target analyte (e.g., cell surface or intracellular proteins) in the biological sample. In some embodiments, the staining includes a chemical stain such as hematoxylin and eosin (H&E) or periodic acid-schiff (PAS). In some embodiments, significant time (e.g., days, months, or years) can elapse between staining and/or imaging the biological sample and performing analysis.

VI. Methods for Determining a Location of a Target Analyte

Provided herein are methods for determining a location of a target analyte in a biological sample that include: (a) contacting a plurality of analyte capture agents (e.g., any of the analyte capture agents described herein) to the biological sample, where an analyte capture agent of the plurality of analyte capture agents comprises an analyte binding moiety barcode (e.g., any of the analyte binding moiety barcodes described herein), an analyte capture sequence (e.g., any of the analyte capture sequences described herein), and an analyte binding moiety (e.g., any of the analyte binding moieties described herein) that binds specifically to the target analyte; (b) disposing the biological sample onto an array (e.g., any of the arrays described herein), where the array has a first area (e.g., any of the first areas described herein) covered by the biological sample and a second area (e.g., any of the second areas described herein) not covered by the biological sample, where the array comprises a plurality of capture probes, where a capture probe of the plurality comprises a spatial barcode (e.g., any of the spatial barcodes described herein) and a capture domain (e.g., any of the capture domains described herein) that binds specifically to the analyte capture sequence; (c) contacting the second area of the array with a solution comprising a diffusion-restricted nuclease (e.g., any of the diffusion-restricted nucleases described herein); (d) removing the diffusion-restricted nuclease from the second area of the array (e.g., using any of the methods for removing the diffusion-restricted nucleases described herein); and (e)

determining (i) all or a portion of the sequence of the spatial barcode, or a complement thereof, and (ii) all or a portion of the sequence of the analyte binding moiety barcode, or a complement thereof, and using the sequences of (i) and (ii) to determine the location of the target analyte in the biological sample.

VII. Methods for Decreasing the Background Binding of a Target Nucleic Acid or Target Analyte Provided herein are methods for decreasing background binding of a target nucleic acid on an array that include: (a) disposing a biological sample onto an array (e.g., any of the arrays described herein), wherein the array has a first area (e.g., any of the first areas described herein) covered by the biological sample and a second area (e.g., any of the second areas described herein) not covered by the biological sample, wherein the array comprises a plurality of capture probes (e.g., any of the capture probes described herein), wherein a capture probe of the plurality of capture probes comprises a spatial barcode (e.g., any of the spatial barcodes described herein) and a capture domain (e.g., any of the capture domains described herein); (b) contacting the second area of the array with a solution comprising a diffusion-restricted nuclease (e.g., any of the diffusion-restricted nucleases described herein), (c) removing the diffusion-restricted nuclease from the second area of the array (e.g., using any of the methods for removing the diffusion-restricted nucleases described herein); and (d) permeabilizing the biological sample (e.g., using any of the methods for permeabilizing a biological sample described herein), such that the capture domain binds to the target nucleic acid in the first area, thereby decreasing the background binding of a target nucleic acid on the array. Some embodiments further include: (e) (e) determining (i) all or a portion of the sequence of the spatial barcode, or a complement thereof, and (ii) all or a portion of the sequence of the target nucleic acid, or a complement thereof, and using the sequences of (i) and (ii) to determine the location of the target nucleic acid in the biological sample.

Provided herein are methods for decreasing background binding of a target analyte on an array that include: (a) contacting a plurality of analyte capture agents (e.g., any of the analyte capture agents described herein) to the biological sample, wherein an analyte capture agent of the plurality of analyte capture agents comprises an analyte binding moiety barcode (e.g., any of the analyte binding moiety barcodes described herein), an analyte capture sequence (e.g., any of the analyte capture sequences described herein), and an analyte binding moiety (e.g., any of the analyte binding moieties described herein) that binds specifically to the target analyte; (b) disposing the biological sample onto an array (e.g., any of the arrays described herein), wherein the array has a first area (e.g., any of the first areas described herein) covered by the biological sample and a second area (e.g., any of the second areas described herein) not covered by the biological sample, wherein the array comprises a plurality of capture probes, wherein a capture probe of the plurality comprises a spatial barcode (e.g., any of the spatial barcodes described herein) and a capture domain (e.g., any of the capture domains described herein) that binds specifically to the analyte capture sequence; (c) contacting the second area of the array with a solution comprising a diffusion-restricted nuclease (e.g., any of the diffusion-restricted nucleases described herein); (d) removing the diffusion-restricted nuclease from the second area of the array (e.g., using any of the methods for removing the diffusion-restricted nucleases described herein), and (e) permeabilizing the biological sample (e.g., using any of the methods for permeabilizing a biological sample described herein), such that the capture domain binds to the analyte capture sequence in the first area, thereby decreasing the background binding of a target analyte on the array. In some embodiments, the methods further include: (f) determining (i) all or a portion of the sequence of the spatial barcode, or a complement thereof, and (ii) all or a portion of the sequence of the analyte binding moiety barcode, or a complement thereof, and using the sequences of (i) and (ii) to determine the location of the target analyte in the biological sample. In some embodiments of these methods, step (a) is performed before step (b). In some embodiments of these methods, step (b) is performed before step (a).

Figure 2:
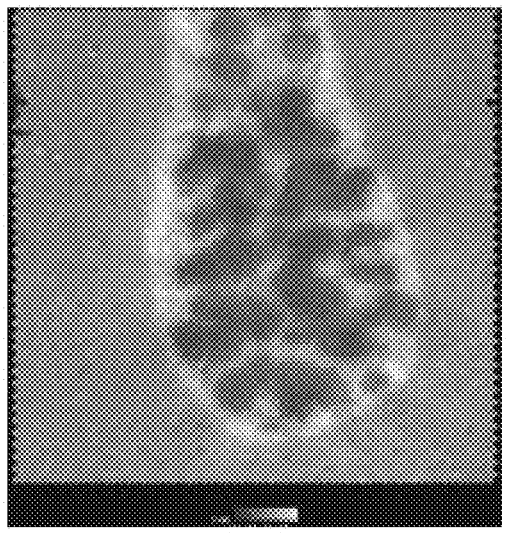
FIG. 2 shows an example of background signal resulting from protein in an area of an array where a spleen tissue sample had not been placed.

Provided herein are methods for decreasing the background binding of a target analyte on a spatial array. For example, as seen in FIGS. 1 and 2, the tissue sections are surrounded by, in these figures, background fluorescence. One cause of the background fluorescence could be a result of target analytes passively diffusing from the tissues and binding to the capture domains of the capture probes that are around the tissue (e.g., a second area of the array). The methods provided herein provide for the digestion, complete or partial, of the nucleic acid capture probes that are not under the biological sample (e.g., the first area). It is contemplated that by completely or partially rendering the capture probe domains adjacent to the biological sample inoperable (e.g., via digestion with an endonuclease or exonuclease, or both), binding of target analytes will be minimized or eliminated, thereby decreasing background on the spatial array. As such, methods for decreasing background on a spatial array comprise a biological sample disposed on a spatial array, wherein the spatial array has a first area covered by the biological sample and a second area not covered by the biological sample, wherein the spatial array comprises a plurality of capture probes, wherein a capture probe of the plurality of capture probes comprises a spatial barcode and a capture domain. The second area of the array is covered with a solution comprising a diffusion-restricted nuclease (any of the nucleases as described herein restricted by any means described herein), which is allowed to be in contact with the second area for a period of time to completely or partially digest all or a portion of the capture probe domain, after which point the nuclease is removed for the spatial array, for example by washing. Following nuclease treatment of the second area of the spatial array, it is contemplated that minimal binding of target analytes from the biological sample will occur. The biological sample can be permeabilized thereby releasing the target analytes from the tissues, target analytes which can bind to the capture domains in the first are and not the second area of the spatial array. The bound analytes can complete the spatial transcriptomics workflow, for example by extension of the capture probe to create complementary sequences to the spatial barcode and (at least) all or a portion of the target analyte sequence, sequences which can be determined to identify the target analyte and its location in the biological sample.

VIII. Kits

Also provided herein are kits that include: an array comprising a plurality of capture probes (e.g., any of the exemplary capture probes described herein), where a capture probe of the plurality of capture probes comprises a spatial barcode (e.g., any of the exemplary spatial barcodes described herein) and a capture domain (e.g., any of the exemplary capture domains described herein); and a diffusion-restricted nuclease (e.g., any of the exemplary diffusion-restricted nucleases described herein).

Also provided herein are kits that include: a plurality of analyte capture agents (e.g., any of the exemplary analyte capture agents described herein), where an analyte capture agent of the plurality of analyte capture agents comprises an analyte binding moiety barcode (e.g., any of the exemplary analyte binding moiety barcodes described herein), an analyte capture sequence (e.g., any of the exemplary analyte capture sequences described herein), and an analyte binding moiety (e.g., any of the exemplary analyte binding moieties described herein) that binds specifically to a target analyte; an array comprising a spatial barcode (e.g., any of the exemplary spatial barcodes described herein) and a capture domain (e.g., any of the exemplary capture domains described herein) that binds specifically to the analyte capture sequence; and a diffusion-restricted nuclease (e.g., any of the exemplary diffusion-restricted nucleases described herein).

In some embodiments of any of the kits described herein, the diffusion-restricted nuclease degrades single-stranded nucleic acids. In some embodiments of any of the kits described herein, the diffusion-restricted nuclease degrades double-stranded nucleic acids. In some embodiments of any of the kits described herein, the diffusion-restricted nuclease is covalently linked to a bead (e.g., any of the exemplary beads described herein). In some embodiments of any of the kits described herein, the diffusion-restricted nuclease is covalently linked to a particle (e.g., any of the exemplary particles described herein). In some embodiments of any of the kits described herein, the diffusion-restricted nuclease is covalently linked to a polymer (e.g., any of the exemplary polymers described herein, such as a polyethylene glycol). In some embodiments of any of the kits described herein, the diffusion-restricted nuclease is an endonuclease. In some embodiments of any of the kits described herein, the diffusion-restricted nuclease is an exonuclease (e.g., a 3' to 5' exonuclease). In some embodiments of any of the kits described herein, the exonuclease is a DNAse. In some embodiments of any of the kits described herein, the array comprises a slide or a bead array.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining a location of a target nucleic acid in a biological sample disposed onto an array, wherein the array comprises a first area covered by the biological sample and a second area not covered by the biological sample, wherein the array comprises a plurality of capture probes affixed to a substrate, wherein each capture probe of the plurality of capture probes comprises a spatial barcode and a capture domain, the method comprising:
   (a) selectively contacting the second area of the array with a diffusion-restricted nuclease;
   (b) removing the diffusion-restricted nuclease from the second area of the array;
   (c) after (a) and (b), permeabilizing the biological sample, such that the target nucleic acid migrates from the biological sample and binds to a capture domain of a capture probe in the first area of the array; and
   (d) determining (i) a sequence of a spatial barcode of the capture probe in the first area of the array, or a complement thereof, and (ii) all or a portion of a sequence of the target nucleic acid, or a complement thereof, and using the sequences of (i) and (ii) to determine the location of the target nucleic acid in the biological sample.

2. The method of claim 1, wherein the diffusion-restricted nuclease degrades single-stranded or double-stranded nucleic acids.

3. The method of claim 1, wherein the diffusion-restricted nuclease is covalently linked to a bead, a particle, or a polymer.

4. The method of claim 1, wherein the diffusion-restricted nuclease is an endonuclease or an exonuclease.

5. The method of claim 1, wherein the removing in (b) comprises washing.

6. The method of claim 1, wherein the array comprises a slide or the array is a bead array.

7. The method of claim 1, wherein the determining in (d) comprises sequencing (i) the sequence of the spatial barcode of the capture probe in the first area of the array, or a complement thereof, and (ii) all or a portion of the sequence of the target nucleic acid, or a complement thereof.

8. The method of claim 1, wherein the determining in (d) comprises extending the capture probe in the first area of the array using the target nucleic acid as the template.

9. The method of claim 1, wherein the biological sample is a tissue section.

10. A method for decreasing background binding of a target nucleic acid in a biological sample on an array, the method comprising:
    (a) disposing the biological sample onto the array, wherein the array comprises a first area covered by the biological sample and a second area not covered by the biological sample, wherein the array comprises a plurality of capture probes affixed to a substrate, wherein each capture probe of the plurality of capture probes comprises a spatial barcode and a capture domain;
    (b) selectively contacting the second area of the array with a diffusion-restricted nuclease,
    (c) removing the diffusion-restricted nuclease from the second area of the array; and
    (d) after (a), (b), and (c), permeabilizing the biological sample, such that the target nucleic acid migrates from the biological sample and binds to a capture domain of a capture probe in the first area of the array, thereby decreasing the background binding of the target nucleic acid on the array.

11. The method of claim 10, further comprising determining (i) a sequence of a spatial barcode of the capture probe in the first area of the array, or a complement thereof, and (ii) all or a portion of a sequence of the target nucleic acid, or a complement thereof, and using the sequences of (i) and (ii) to determine the location of the target nucleic acid in the biological sample.

12. The method of claim 11, wherein the determining comprises sequencing (i) the sequence of the spatial barcode of the capture probe in the first area of the array, or a complement thereof, and (ii) all or a portion of the sequence of the target nucleic acid, or a complement thereof.

13. The method of claim 11, wherein the determining comprises extending the capture probe in the first area of the array using the target nucleic acid as the template.

14. The method of claim 10, wherein the diffusion-restricted nuclease degrades single-stranded or double-stranded nucleic acids.

15. The method of claim 10, wherein the diffusion-restricted nuclease is covalently linked to a bead, a particle, or a polymer.

16. The method of claim 10, wherein the diffusion-restricted nuclease is an endonuclease or an exonuclease.

17. The method of claim 10, wherein the removing in (c) comprises washing.

18. The method of claim 10, wherein the array comprises a slide or the array is a bead array.

19. The method of claim 10, wherein (a) and (b) are performed at the same time.

20. The method of claim 10, wherein the biological sample is a tissue section.

\* \* \* \* \*

UNITED STATES PATENT AND TRADEMARK OFFICE
CERTIFICATE OF CORRECTION

PATENT NO. : 12,365,942 B2  
APPLICATION NO. : 17/147874  
DATED : July 22, 2025  
INVENTOR(S) : Marlon Stoeckius Page 1 of 1

It is certified that error appears in the above-identified patent and that said Letters Patent is hereby corrected as shown below:

On the Title Page

Column 1 (Inventor), Line 1, delete "(CH)" and insert -- (SE) --.

Signed and Sealed this  
Ninth Day of September, 2025

Coke Morgan Stewart  
*Acting Director of the United States Patent and Trademark Office*